(12) United States Patent
Benech et al.

(10) Patent No.: US 11,561,201 B2
(45) Date of Patent: Jan. 24, 2023

(54) DEVICE AND METHOD FOR DETERMINING THE ELASTICITY OF SOFT-SOLIDS

(71) Applicant: UNIVERSIDAD DE LA REPUBLICA, Montevideo (UY)

(72) Inventors: Nicolás Benech, Montevideo (UY);
Gustavo Grinspan, Montevideo (UY);
Sofía Aguiar, Montevideo (UY);
Carlos Negreira, Montevideo (UY)

(73) Assignee: UNIVERSIDAD DE LA REPUBLICA, Montevideo (UY)

( * ) Notice: Subject to any disclaimer, the term of this patent is extended or adjusted under 35 U.S.C. 154(b) by 0 days.

(21) Appl. No.: 16/646,396

(22) PCT Filed: Oct. 30, 2018

(86) PCT No.: PCT/BR2018/050395
§ 371 (c)(1),
(2) Date: Mar. 11, 2020

(87) PCT Pub. No.: WO2019/084646
PCT Pub. Date: May 9, 2019

(65) Prior Publication Data
US 2020/0271624 A1    Aug. 27, 2020

Related U.S. Application Data

(60) Provisional application No. 62/579,262, filed on Oct. 31, 2017.

(51) Int. Cl.
*G01N 29/07*    (2006.01)
*G01N 29/52*    (2006.01)
(Continued)

(52) U.S. Cl.
CPC ............ *G01N 29/07* (2013.01); *A61B 5/01* (2013.01); *A61B 5/4519* (2013.01); *A61B 5/74* (2013.01);
(Continued)

(58) Field of Classification Search
CPC .... G01N 29/07; G01N 29/2437; G01N 29/42; G01N 29/4436; G01N 29/52;
(Continued)

(56) References Cited

U.S. PATENT DOCUMENTS

2013/0305831 A1* 11/2013 Zimmermann ......... B23P 19/00
                                                          73/708
2014/0193547 A1*  7/2014 Brown .................... A23K 10/24
                                                          426/104
(Continued)

OTHER PUBLICATIONS

Grinspan G A et al, Optimization of a surface wave elastography method through diffraction and guided waves effects characterization, Journal of Physics, Conference Series, May 10, 2016, Jan. 2014, vol. 705, IOP Publishing, Pulished Online.
(Continued)

*Primary Examiner* — Suman K Nath
(74) *Attorney, Agent, or Firm* — Muncy, Geissler, Olds & Lowe, P.C.

(57) ABSTRACT

The invention comprises a device and method to estimate the elasticity of soft elastic solids from surface wave measurements. The method is non-destructive, reliable and repeatable. The final device is low-cost and portable. It is based in audio-frequency shear wave propagation in elastic soft solids. Within this frequency range, shear wavelength is centimeter sized. Thus, the experimental data is usually collected in the near-field of the source. Therefore, an inversion algorithm taking into account near-field effects was developed for use with the device. Example applica-
(Continued)

tions are shown in beef samples, tissue mimicking materials and in vivo skeletal muscle of healthy volunteers.

2 Claims, 18 Drawing Sheets

(51) Int. Cl.
A61B 5/01 (2006.01)
A61B 5/00 (2006.01)
G01C 3/02 (2006.01)
G01K 13/00 (2021.01)
G01L 5/00 (2006.01)
G01N 29/24 (2006.01)
G01N 29/42 (2006.01)
G01N 29/44 (2006.01)

(52) U.S. Cl.
CPC ............... *G01C 3/02* (2013.01); *G01K 13/00* (2013.01); *G01L 5/00* (2013.01); *G01N 29/2437* (2013.01); *G01N 29/42* (2013.01); *G01N 29/4436* (2013.01); *G01N 29/52* (2013.01); *A61B 2562/0247* (2013.01); *A61B 2562/0252* (2013.01); *G01N 2291/011* (2013.01); *G01N 2291/02827* (2013.01); *G01N 2291/0423* (2013.01); *G01N 2291/106* (2013.01)

(58) Field of Classification Search
CPC .... G01N 29/323; G01N 29/326; G01N 29/46; G01N 29/075; G01N 29/041; G01N 29/024; G01N 2291/011; G01N 2291/02827; G01N 2291/0423; G01N 2291/106; G01N 2291/02483; G01N 2291/103; G01N 2291/0235; G01N 2291/012; A61B 5/01; A61B 5/4519; A61B 5/74; A61B 5/0051; A61B 5/0053; A61B 2562/0247; A61B 2562/0252; A61B 9/00; A61B 8/485; G01C 3/02; G01K 13/00; G01L 5/00
See application file for complete search history.

(56) References Cited

U.S. PATENT DOCUMENTS

2017/0030877 A1\* 2/2017 Miresmailli ........ A01M 21/043
2017/0306608 A1\* 10/2017 Goldberg .............. G01F 23/164

OTHER PUBLICATIONS

Benech N et al, In vivo assessment of muscle mechanical properties using a low-cost surface wave method, Proceedings of the 2012 IEEE International Ultrasonics Symposium, Oct. 2012, pp. 2571-2574, Published on CD-Rom.

Zhang X et al, Noninvasive ultrasound image guided surface wave method for measuring the wave speed and estimating the elasticity of lungs: A feasibility study, Ultrasonics, Oct. 23, 2010, pp. 289-295, vol. 51—Issue 3, Elsevier B.V., Published online.

Zhang X, A surface wave elastography technique for measuring tissue viscoelastic properties, Medical Engineering & Physics, Apr. 2017, pp. 111-115, vol. 42, Elsevier B.V., Published online.

\* cited by examiner

DEVICE AND METHOD FOR DETERMINING THE ELASTICITY OF SOFT-SOLIDS

REFERENCES CITED

U.S. patents

| U.S. Pat. No. 6,619,423 B2 | September 2003 | Courage |
| U.S. Pat. No. 9,044,192 B2 | June 2015 | Geenleaf et al |

INTERNATIONAL PATENTS

| EP 0329817 B1 | August 1992 | Sarvazyan et al. |
| UY 36047 | March 2015 | Benech et al. |

OTHER REFERENCES

F. Carduza, G. Sanchez, G. Grigioni y M Irureta, "Manual de procedimientos para la determinacion de la calidad fisica y sensorial de came bovina", Instituto Nacional de Tecnologia Agropecuaria (INTA), INTA Ediciones, Argentina, 2012.
V. V. Kazarov, B. N. Klochkov, "Low frequency mechanical properties of the soft tissue of the human arm," Biophysics, vol. 34 (4), pp. 742-747, 1989.
X. Zhang, B. Qiang, J. Greenleaf, "Comparison of the surface wave method and the indentation method for measuring the elasticity of gelatin phantoms of different concentrations," Ultrasonics, vol. 51(2), pp. 157-164, 2011.
K. G. Sabra, S. Conti, P. Roux, and W. A. Kuperman, "Passive in vivo elastography from skeletal muscle noise," Applied Physics Letters, vol. 90, pp. 194101-194101-3, 2007.
M. Salman, K. G. Sabra, "Surface wave measurements using a single continuously scanning laser Doppler vibrometer: Application to elastography," Journal of Acoustical Society of America, vol. 133 (3), pp 1245-1254, 2013.
N. Benech, S. Aguiar, G. A. Grinspan, J. Brum, C. Negreira, "In vivo Assessment of Muscle Mechanical Properties Using a Low-cost Surface Wave Method," Proceedings of the IEEE Ultrasonics Symposium, vol. 2012, pp. 2571-2574, 2012.
L. Landau and E. Lifshitz, Theory of elasticity, Pergamon Press, New York, 1970.
E. Diuelesaint and D. Royer, "Elastic waves in solids", Wiley, New York, 1980.
G. Miller and H. Pursey, "The field and radiation impedance of mechanical radiators on the free surface of a semi-infinite isotropic solid", Porc. R. Soc. London Ser A, vol. 223, pp. 521-541, 1954.
J. Brum, J-L. Gennisson, T-M. Nguyen, N. Benech, M. Fink, M. Tanter and C. Negreira, "Application of 1D transient elastography for the shear modulus assessment of thin layered soft tissues: Comparison with supersonic shear imaging", IEEE Trans. Ultras. Ferroelec. Freq. Control, vol. 59 (4), pp. 703-713, 2012.
N. Benech, C. Negreira y G. Brito, "Elastografia ultrasonica para evaluacion de la terneza de carne vacuna" en Herramientas tecnologicas aplicadas a calidad y diferenciacion de la carne, 29-44, G. Grigione y F. Paschetta, coordinadoras, PROCISUR publicaciones, Montevideo, 2012.
N. Benech, J. Brum, G. Grinspan, S. Aguiar and C. Negreira, "Analysis of the transient surface wave propagation in soft solids elastic plates", J. Acoust. Soc. Am. Vol. 142, 2919-2932, 2017.

FIELD OF THE INVENTION

The present invention relates to the fields of elastodynamics and elastography. More specifically, the present invention provides a method and device for estimating the elastic properties of incompressible elastic solids. The present invention has applications in, but is not limited to, food industry, polymers industry, biomechanics, bioengineering and medicine.

BACKGROUND OF THE INVENTION

Incompressible elastic solids sometimes are also referred to as soft-solids because they are easy to deform. Elastic properties of soft-solids are of great interest in food industry (meat, beef, cheese, fruits), polymer industry (rubber, soft polymers) and medicine (muscles and soft tissues in general). Some of the existing methods to determine elasticity of soft-solids are destructive (Tensile tests, Warner-Bratzler shear force, WBSF, test). Non-destructive methods include ultrasound elastography and surface wave elastography.

Ultrasound elastography is capable of mapping locally the elasticity in soft-tissues. Another advantage is that the method estimates the elasticity of tissue in a direct way, without needing inversion algorithms. Ultrasound elastography needs a dedicated ultrasound scanner which is onerous. Moreover, ultrasound elastography has some limitations. For example, it does not work in materials without sound scatterers inside (termed as speckle-less materials). In addition, it is not useful in materials where ultrasound frequencies are highly attenuated (food industry in general like cheese, yoghurt and fruits). Thus, ultrasound elastography is limited to some applications in medicine.

Surface wave methods have been proposed as an alternative to ultrasound elastography. These methods have the advantage that they are low-cost compared with ultrasound. However, surface waves have not a direct relation with elasticity and thus, inversion algorithms are needed to properly estimate the elasticity. Most authors assume Rayleigh surface wave propagation. In such case, the inversion algorithm is simple. However, in most practical cases the conditions for Rayleigh wave propagation are not achieved. Thus, the elasticity estimation is biased due to the inversion algorithm. Other authors assume guided wave propagation in thin plates like skin or arteries. However, guided waves are affected by near-field effects that are not negligible in soft-solids. Most surface wave methods are based on laser vibrometry to scan de displacement field over the surface. A major drawback is that the elasticity estimation is not performed in real-time. These methods use a single measurement device, which scans over the surface of the sample. Thus, they can not follow rapid changes in elasticity like muscle activation.

The present invention provides a non-destructive device and a reliable method to estimate the elasticity of soft-solids samples using surface waves. The proposed method overcomes some drawbacks found in the previous works as described above. Thus, the present invention provides an alternative elastographic device and method, which is non-destructive, low-cost, real-time, quantitative and repeatable.

BRIEF DESCRIPTION OF THE INVENTION

These and other objectives of the invention are met through a device and method for determining the elasticity of soft-solids. According to a first aspect, the invention comprises a device for determining the elasticity of soft-solids which comprises a wave source, a shaft coupled by one of its ends to the wave source and which bears a head piece in its opposite end, a plurality of vibration sensors linearly arrayed to each other, and an analogical-to-digital converter connected to the vibration sensors and to a processor. In the device of the invention, the face of head piece opposed to the shaft and the plurality of vibration sensors are substantially on a same plane on the same side of the device, and the axis of the shaft is normal to the plane containing the sensors and head of the shaft.

In a particular embodiment of the invention, the vibration sensors are piezoelectric sensors. In another particular embodiment of the invention, alone or in combination with any of the above or below embodiments, the sensors are four.

In another particular embodiment of the invention, alone or in combination with any of the above or below embodiments, the face of head piece opposed to the shaft (wave source) has the shape of a rectangle with its long side perpendicular to the line connecting the shaft and the sensors and its short side parallel to the said line.

In another particular embodiment of the invention, alone or in combination with any of the above or below embodiments, the device further comprises a temperature sensor.

In another particular embodiment of the invention, alone or in combination with any of the above or below embodiments, the device further comprises a pressure sensor. In a more particular embodiment of the invention, the pressure sensor consists of a load cell connected to a voltage divider circuit with comparator. The pressure sensor can be connected to led light indicators for indicating to the user if the correct amount of pressure is being applied to the sample to be measured.

In another particular embodiment of the invention, alone or in combination with any of the above or below embodiments, the device further comprises a distance sensor. In a more particular embodiment of the invention, the distance sensor is an infrared sensor.

According to a second aspect, the invention relates to a method for determining the elasticity of a soft-solid, the method comprising the steps of:
a) using a wave source for exciting low-amplitude audible frequency waves in a selected location of a free surface of the soft-solid whose elasticity is to be determined,
b) recording the time-traces of the surface displacement with a plurality of contact vibration sensors that are linearly arranged,
c) computing the phase velocity of the surface wave by estimating the phase-shift between sensors and a reference signal sent to the source,
d) converting the phase velocity computed in step c to an elasticity value by using an inversion algorithm.

In one embodiment of the method of the invention, alone or in combination with any of the above or below embodiments, an analogic-to-digital converter receives analogical information from the sensors, transforms it into digital information, and transmits that digital information to a processor.

In another particular embodiment of the method of the invention, alone or in combination with any of the above or below embodiments, the calculated elasticity value is shown into a display.

STATE OF THE ART

1) EP0329817B1—date of filing: Mar. 3, 1988

This patent claims a non invasive acoustic testing of elasticity of soft biological tissues. In its preferred embodiment, it measures the velocity of the waves by means of a probe with one transmitting and two receiving piezotransducers, the receiving transducers being placed symmetrically with respect to the transmitter, being that this allows for the differential amplification of the received acoustic signals. These piezotransducers are mounted onto the probe by means of acoustic delay lines in the form of hollow thin-wall metallic shafts, long enough to delay the acoustic signal passing from transmitter to receiver through the body of the probe. There is also a needle contact (not a line source as in ours), a spring and a tubular contact. Converting the value of the elapsed time of the surface wave between the points of irradiation and reception is indicative of the elasticity of the tissue in the direction of wave propagation. All this is completely different—in principle and in physical construction—from our invention, which is based on surface waves and their phase shift, besides having an analog/digital conversion system and pressure sensor which are fundamentally different from this invention. Taking into consideration that shear waves travel through soft tissues approximately 1000 times slower and attenuate approximately 10000 times faster than longitudinal conventional ultrasound waves, both inventions are almost in different fields (radiographics.rsna.org, May-June 2017).

2) U.S. Pat. No. 9,044,192—date of filing: Apr. 3, 2009

This patent shows numerous and significant differences with the current invention, such as: it is useful only for soft tissue in living animals, not for soft solids in general as the current invention; it is based in a viscoelastic model, and must thus determine two factors, one elastic and one viscous, while the current invention is a purely elastic model and thus only an elastic parameter is determined; it includes multilayered tissues, while the current invention does not; phase velocity is measured by means of linear regression or phase vs. distance, while in the current invention this hypothesis is not present; it is based on distant field equations (although it is not said explicitly) since normal propagation modes are used, while in the current invention only the near field counts; it is only applied to isotropic tissues—although in claim 13 anisotropic tissues are considered, nothing in the Memory justifies such claim and there is no mention of how to quantify parameters in such a case—while in the current invention the device is used on isotropic and anisotropic (transversally isotropic) soft solids, furthermore in the current invention, a method of how to quantitatively obtain the parameters is described for both cases (isotropic and anisotropic); it does not include temperature corrections (since measurements are always taken at the same temperature) while the current invention does; it uses remote sensors (ultrasound or laser vibrometry), while the current invention uses contact sensors. The use of far-field equations causes a bias in the measurement results, bias which depends on frequency. This is not true for the current invention since, upon using near field equations, all the tissue and not only the superficial layers are accurately measured. Given all these substantial differences, patent U.S. Pat. No. 9,044,192 is only useful for medical purposes of inner organs, a field completely different from the one aimed at in the current invention.

3) UY36047—date of filing: Mar. 27, 2015

This patent and the one herewith filed are based on surface waves, but are significant differences, as follows:

In patent UY36047 only isotropic solids were considered, while in the current one anisotropic solids are also included.

In patent UY36047 only surface waves of the Raleygh type were considered, while in the current one the effects of near field which include various surface waves are included.

In patent UY36047 was centered in correcting the effects of diffraction and guided waves, while in the current one both the source and the sensors have been modified so as to make it unnecessary to correct said effects.

Patent UY36047 did not take into consideration temperature changes, while the current one does.

Patent 11Y35047 did not take into consideration modifications of the reported elasticity value due to the pressure exerted by the device. In the current application this effect is indeed taken into consideration by means of a pressure sensor.

Patent UY36047 did not establish or specify useful frequency limits, while the current one does.

It is our contention that, due to these significant differences, none of these patents is a useful antecedent to question either the novelty of the inventive step of the current invention.

DETAILED DESCRIPTION OF THE INVENTION

The elements making up the equipment of the present invention are described below, with the numbers with which they appear in the figures.

1—Wave source with a coupled shaft
2—Vibration sensors
3—Outputs to the analog to digital (A/D) signal converter
4—Audio amplifier
5—Start button
6—Temperature sensor
7—Pressure sensor
8—Rod attached to load cell (pressure sensor)
9—Led lights indicator
10—Bubble level
110—Distance sensor
12—Holding handle
13—Cushioning sponge
14—Holding brace
15—Trigger
16—Computer
17—Head piece with rectangular shape The method is based in the following steps: 1) Using a wave source (1), excite low-amplitude audible frequency waves in a selected location of a free surface of the sample. The exciting frequency as well as the number of cycles excited are user-controlled. They can be selected in order to optimize the results for the particular application. 2) Record the time-traces of the surface displacement using contact vibration sensors arranged in a linear array along the free surface of the sample (2). 3) Compute the phase velocity of the surface wave by estimating the phase-shift between sensors and source. 4) Use an inversion algorithm to convert the phase velocity computed in the previous step to a meaningful elasticity value (Block diagram FIG. 10). 5) Report the result in a display.

The device also comprises an A/D converter (3) to digitize the analog signals from the linear array of surface vibration sensors and a processor to compute the time-shifts between sensors and perform the data processing (15). Detailed features of the present invention will be described in the following paragraphs.

The processing algorithm estimates the phase shift between the signals recorded by the linear array of vibration sensors and the reference signal sent to the source. Thus, the first step is to apply a band-pass filter centered on the source's frequency with a bandwidth between 30% and 50%. This allows eliminating unwanted frequencies that can affect the estimates. Then, the phase shift between the recorded signals and the reference signal is computed at a selected frequency within the bandwidth by Fourier transform. The phase shift is converted to time delay by dividing the phase shift between the corresponding angular frequency. This procedure allows the estimation of the surface wave velocity since the distance source-sensor is known (distances d and d' in FIG. 1).

The operation of the method does not present limitations concerning to the working frequency. However, depending on frequency, it may be necessary to correct the computed value taking into account guided wave propagation. Therefore, the main objective of this invention is to apply correction algorithms designed to automatically correct the incidence of guided waves. Thus, the invention provides a quantitative and reliable tool to estimate the shear wave velocity of tested samples. The shear wave velocity is related to an elastic modulus depending on the type of solid being tested.

The equipment comprising the present invention is constituted by an external wave source having a coupled shaft (1). The operation frequency range as well as the number of cycles are selected by the application for which the invention is intended to be used. That source should vibrate normally to a free surface of the sample in order to excite mainly the vertical component of the surface waves. The waves thus generated will be recorded by a linear arrangement of vibration sensors (2) (e.g. piezoelectric sensors, accelerometers, resistive sensors, microphones, etc.), which are placed along the free surface of the sample. These sensors record the vertical component of the vibrations (FIG. 1). FIG. 1 shows a non-limiting example of piezoelectric sensor, constituted by a PVDF flexible piezoelectric film, possessing a mass on the end and a small extension attached to it. The attached mass offers a great sensitivity to these sensors to record the surface vibrations, keeping their effective area (and thus the signal/noise ratio) but with a minimum contact area. Therefore, the sensors are point-like and diffraction effects in the velocity estimation of surface waves are avoided. The analog signal of each sensor is digitized by an analog to digital (A/D) signal converter (3), being subsequently transferred to a computer (16) for processing. See FIG. 16 which illustrates an example of the time trace of a recorded signal. The raw (up) and filtered (down) signals are shown.

In order to the device of the present invention to work properly, the source must be aligned with the array of sensors, which must avoid contact with each other (FIG. 1). An audio amplifier (4) is employed to excite the vibrator. The assembly on which the sensors are arranged may cover different alternatives. As non-exclusive examples of the above, the sensors can be arranged on a plate which holds them in the correct configuration (FIG. 3A). The plate is positioned on the surface of the sample either by a holding brace (FIG. 3D) or by attaching it to a holder with a holding handle (FIG. 3A-3C). On the other hand, in different modalities or realizations of the invention, there is the possibility of including other sensors, which allow to control and standardize the measurement in function of external variables that can influence the results. Thus, the equipment can include a temperature sensor (6), that allows the method to estimate the elastic modulus as function of temperature (FIG. 11). The equipment may also include a pressure sensor (7), consisting of a load cell connected to a voltage divider circuit with comparator and led indicator lights (8). This allows the user to control the pressure exerted on the medium during the measurements, as well as to quickly adjust the pressure when it is above or below the optimum established range. Also, a bubble level (9) attached next to the led indicator lights allows the user to level the pressure exerted on the medium so that this will be uniform in the anterior-posterior direction. In addition, the equipment may also include a distance sensor (10), typically infrared but not limiting, for measuring the thickness of the medium. Knowing the samples' thickness allows correcting the surface wave velocity by guided waves effect as described in the theoretical section.

Based on the above, the operation of the equipment described in the present invention has the advantage of being based on a few basic directions. In a preferred realization or modality, the equipment comprises four vibration sensors arranged in a linear array. Likewise, the vibrator should be placed on the surface of the soft solid whose elasticity is to be measured, being placed on the external side of the array (FIG. 1). The vibration should be normal to the surface in order to excite the vertical component of surface waves. In this way, the signals will be received and processed by the equipment, which will provide the corresponding elasticity value in real time via a monitor or display.

DESCRIPTION OF THE FIGURES

FIG. 3D is a strap for attaching the sensors to live muscles (14).

THEORY OF OPERATION

Figure 1:
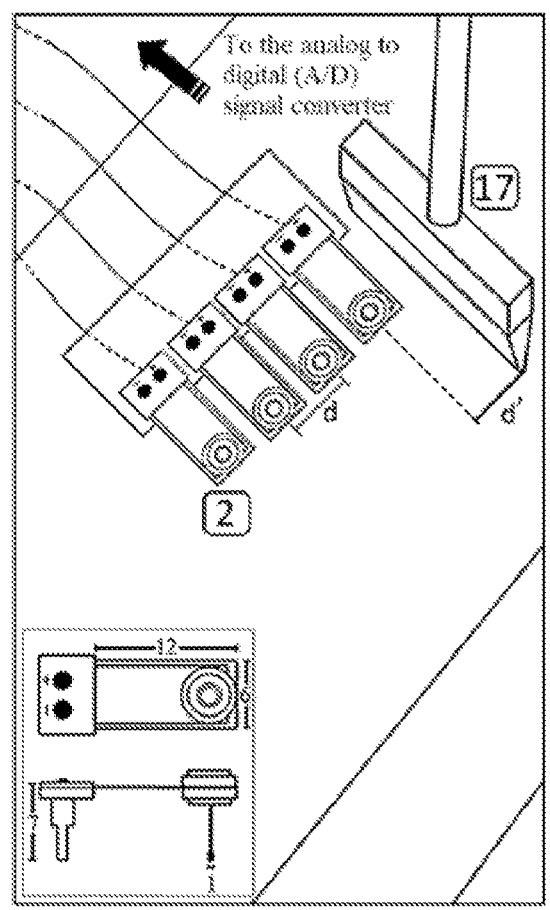
FIG. 1: shows a linear arrangement of vibration sensors (2) and the head piece (17). This is a non-limiting example of piezoelectric vibration sensor, constituted by a PVDF flexible piezoelectric film, it has a mass on the end with a small extension attached to it. Dimensions in millimeters are shown below to the left. The distance d between sensors as well as the distance d' between the source and the first sensor are also displayed.
Figure 2:
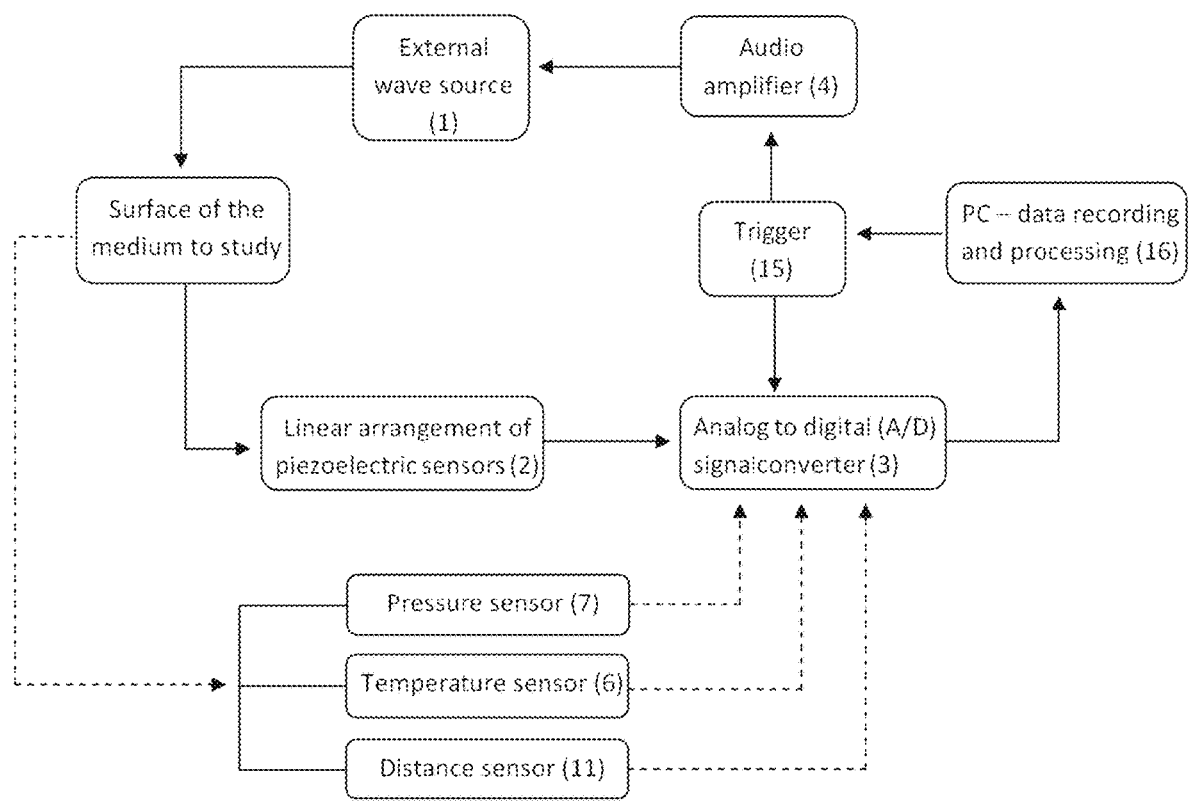
FIG. 2: is a flowchart for obtaining data with the present invention. Dotted lines indicate that pressure sensor, temperature sensor and distance sensor are optional elements.
Figure 3A:
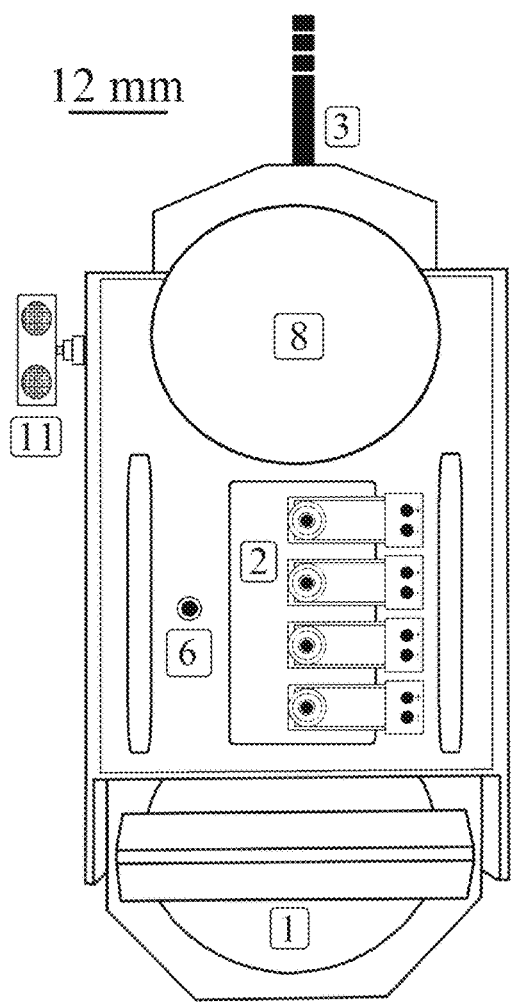
FIG. 3A-3D: shows two alternative assemblies for arranging the vibration sensors on the medium of interest. 3A-3C corresponds to inferior, superior and lateral views, respectively. Scale bar=12 mm.
Figure 3B:
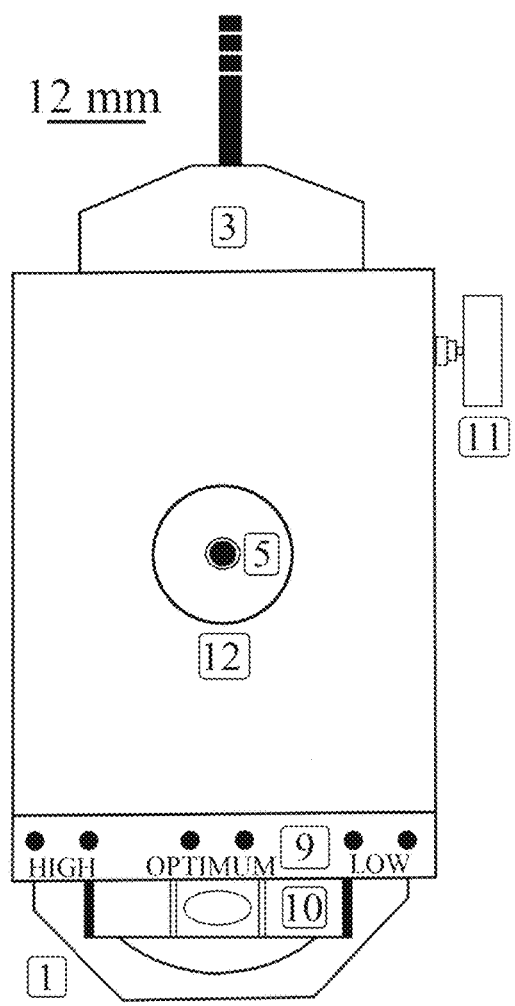
Figure 3C:
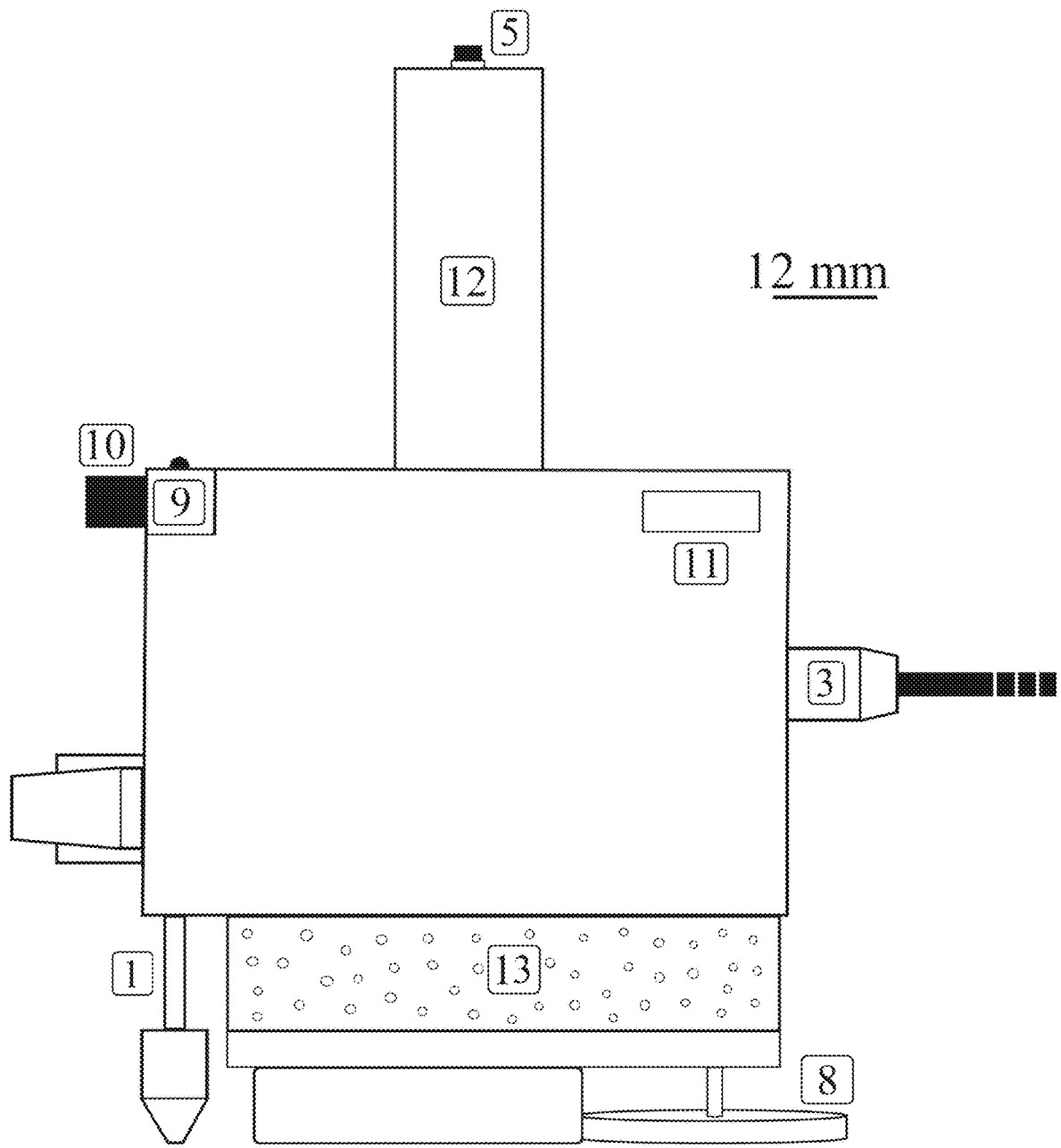
Figure 3D:
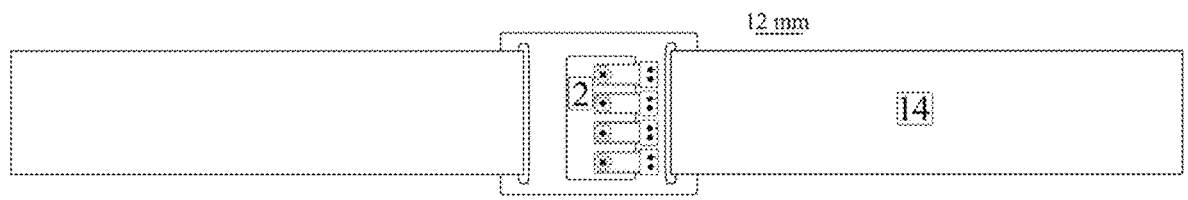

In linear elasticity theory, the stress and strain within an elastic solid are related by the generalized Hooke's law:

$$\tau_{mj} = C_{mjkl}\epsilon_{kl} \qquad 1$$

where the Einstein's convention over repeated indices apply. In this equation $\tau_{ij}$ is the stress tensor, $\epsilon_{kl}$ is the strain tensor defined as $$\epsilon_{kl} = \frac{1}{2}\left(\frac{\partial u_k}{\partial u_l} + \frac{\partial u_l}{\partial u_k}\right),$$

$u_k$ is the k=1, 2, 3 component of the displacement field and $C_{mjkl}$ is the stiffness tensor. It has 81 ($3^4$) elements representing elastic constants. However, since $\tau_{mj}=\tau_{jm}$ and $\epsilon_{kl}=\epsilon_{lk}$, this number reduces to 36 independent coefficients. Moreover, since the symmetry of the derivative of the strain energy with respect to the strain tensor, this number reduces further to 21 independent coefficients. Thus, the 21 independent elastic coefficients define the general anisotropic elastic solid. In order to avoid working with a fourth rank tensor, it is usual to represent the independent constants of the stiffness tensor by two indices $\alpha$ and $\beta$ with values 1 to 6 corresponding to a 6×6 array with the following convention:

(11)↔1 (22)↔2 (33)↔3
(23)=(32)↔4 (31)=(13)↔5 (12)=(21)↔6

Thus, $C_{mjkl}=C_{\alpha\beta}$ with $\alpha$ related to (mj) and $\beta$ related to (kl).

The fundamental relation of dynamics applied to this system gives:

$$\rho \frac{\partial^2 u_m}{\partial t^2} = \frac{\partial \tau_{mj}}{\partial x_j} \qquad 2$$

where $\rho$ is the material density. When using the Hooke's law (1) to express the stress tensor, this equation reads:

$$\rho \frac{\partial^2 u_m}{\partial t^2} = C_{mjkl} \frac{\partial^2 u_l}{\partial x_j \partial x_k} \qquad 3$$

which is a system of three second order differential equation accounting for wave propagation in three dimensional anisotropic bodies. Plane wave solutions to this equation are expressed as:

$$u_m = \hat{e}_m F\left(t - \frac{\hat{n}_j x_j}{V}\right) \qquad 4$$

where $\hat{e}_m$ is a unit vector in the direction of particle displacement and is referred as the wave polarization and $\hat{n} = (n_1, n_2, n_3)$ is a unit vector in the direction of wave propagation. Inserting equation (4) into equation (3) gives:

$$\rho V^2 \hat{e}_m = C_{mjkl} n_j n_k \hat{e}_l; \qquad 5$$

Introducing the second rank tensor $\Gamma_{ml} = C_{mjkl} n_j n_k$ this equation becomes the Christoffel equation:

$$\rho V^2 \hat{e}_m = \Gamma_{ml} \hat{e}_l \qquad 6$$

Thus, the polarization and phase velocity of a plane wave propagating in direction $\hat{n}$ are the eigenvector and eigenvalue of the Christoffel tensor $\Gamma_{ml}$ respectively. Since this tensor is symmetric, its eigenvalues are real and its eigenvectors are orthogonal with each other.

Isotropic Solid

For an isotropic solid, the stiffness matrix takes the form:

$$C_{\alpha\beta} = \begin{pmatrix} c_{11} & c_{112} & c_{12} & 0 & 0 & 0 \\ c_{12} & c_{11} & c_{12} & 0 & 0 & 0 \\ c_{12} & c_{12} & c_{11} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & c_{44} \end{pmatrix} \qquad 7$$

where $c_{11} = c_{12} + 2c_{44}$. Thus, an isotropic solid has only two independent elastic constants $c_{12} = \lambda$ and $c_{44} = \mu$ referred as Lame constants. In mechanical engineering literature two other constants are employed, the Young's modulus Y and the Poisson's ratio $\sigma$. They are related to Lamé constants by:

$$Y = \mu \frac{3\lambda + 2\mu}{\lambda + \mu} \qquad 8$$

$$\sigma = \frac{\lambda}{2\lambda + \mu} \qquad 9$$

An incompressible elastic solid is defined as a solid with Poisson's ratio $\sigma \approx \frac{1}{2}$. In terms of Lame constants this means $\lambda \gg \mu$ and thus, $c_{11} \gg c_{44}$. The objective of the present invention when applied to isotropic soft-solids is to estimate the value of $\mu = c_{44}$ from surface waves.

For an isotropic solid, the Christoffel tensor is independent of the propagation direction. It reads:

$$\Gamma_{il} = \begin{pmatrix} c_{44} & 0 & 0 \\ 0 & c_{44} & 0 \\ 0 & 0 & c_{11} \end{pmatrix} \qquad 10$$

Therefore, the eigenvalues are $V_T = \sqrt{c_{44}/\rho}$ (degenerate) and $V_L = \sqrt{c_{11}/\rho}$ corresponding to polarizations perpendicular and parallel to the propagation direction respectively. Thus, $V_T$ is the velocity of transverse or shear waves and $V_L$ is the velocity of longitudinal or compressional waves. Due to the relation $c_{11} \gg c_{44}$, $V_L \gg V_T$ in a soft-solid. If the material density of the sample is known, the value of $c_{44}$ can be estimated by measuring the velocity $V_T$ of shear waves and inverting the first eigenvalue relation written above: $c_{44} = \rho V_T^2$. Thus, the task has changed to estimate $V_T$ from measuring the surface displacement field.

When inserting the stiffness matrix given in equation (7) into the wave equation (3), the wave equation for isotropic solids is obtained. It can be written in vectorial form as:

$$\rho \frac{\partial^2 \vec{u}}{\partial t^2} = (c_{11} - c_{44}) \nabla (\nabla \cdot \vec{u}) + c_{44} \nabla^2 \vec{u} \qquad 11$$

Taking the divergence in the equation above gives:

$$\rho \frac{\partial^2 (\nabla \cdot \vec{u})}{\partial t^2} = c_{11} \nabla^2 (\nabla \cdot \vec{u}) \qquad 12$$

Thus, $\nabla \cdot \vec{u}$ it is an irrotational wave that propagates with velocity $V_L$, i.e., the compressional wave velocity. Let D be a characteristic dimension of the sample being tested (e.g. its length or width). If the excitation frequency $f_0$ of the wave is chosen such that $f_0 \ll V_L/D$, then the wavelength of the irrotational wave $\nabla \cdot \vec{u}$ is much larger than D. Therefore, $\nabla \cdot \vec{u}$ it is approximately constant within the sample and it is possible to write $\nabla(\nabla \cdot \vec{u}) \cong 0$. Under this condition, the wave equation (11) becomes:

$$\rho \frac{\partial^2 \vec{u}}{\partial t^2} \cong c_{44} \nabla^2 \vec{u} \qquad 13$$

That is, low-frequency waves in soft-solids propagate almost as shear waves. This last assertion is true for bulk wave propagation in an infinite solid. If the sample is limited by a free surface, surface waves also propagate.

Without loss of generality, consider a surface wave propagating along the $x_1$ direction. The displacement field is given by:

$$u_m = \psi_m(kx_3) e^{i(\omega t - kx_1)} \qquad 14$$

where m=1,3 and $u_2 \equiv 0$. Inserting (14) into the wave equation (3) and using the stiffness matrix for an isotropic solid (7), gives:

$$(\rho V^2 - c_{11})\psi_1(kx_3) + c_{44}\psi_1''(kx_3) - (c_{12} + c_{44})\psi_3'(kx_3) = 0 \qquad 15$$

$$(\rho V_2 - c_{44})\psi_3(kx_3) + c_{11}\psi_3''(kx_3) - i(c_{12} + c_{44})\psi_1'(kx_3) = 0 \qquad 16$$

where $V=\omega/k$ is the velocity of the surface wave and the primes over the functions indicates derivative with respect to their argument. The solution to this system is given by:

$$\psi_1(kx_3)=A_1 e^{-\chi_1 kx_3}+i\chi_3 A_3 e^{-\chi_3 kx_3} \quad (17)$$

$$\psi_3(kx_3)=-i\chi_1 A_1 e^{-\chi_1 kx_3}+A_3 e^{-\chi_3 kx_3} \quad (18)$$

in which the coefficients $A_1$ and $A_3$ are determined by the mechanical boundary conditions and $$\chi_1 = \sqrt{1-\left(\frac{V}{V_L}\right)^2} \; ; \; \chi_3 = \sqrt{1-\left(\frac{V}{V_T}\right)^2} \quad (19)$$

For a free surface, the relevant boundary conditions at $x_3=0$, are: $\tau_{m3}=0$, where m=1,3. Using (1) and (7), the boundary conditions read:

$$2\chi_1 A_1+i(1+\chi_3^2)A_3=0 \quad (20)$$

$$i(-c_{12}+c_{11}\chi_1^2)A_1+\chi_3(c_{12}-c_{11})A_3=0 \quad (21)$$

In order to avoid the trivial solution, the determinant of the coefficient matrix must be zero. This gives rise to the secular equation for the surface waves:

$$2\chi_1\chi_3(c_{12}-c_{11})+(1+\chi_3^2)(c_{11}\chi_1^2-c_{12})=0 \quad (22)$$

Replacing in this equation the values of $\chi_1$, $\chi_3$, $c_{11}$ and $c_{12}$ in terms of the velocities, the secular equation becomes the well-known Rayleigh equation:

$$\frac{V}{V_T}\left[\left(\frac{V}{V_T}\right)^6-8\left(\frac{V}{V_T}\right)^4+\left(24-\frac{16V_T}{V_L}\right)\left(\frac{V}{V_T}\right)^2-16\left(1-\left(\frac{V_T}{V_L}\right)^2\right)\right]=0 \quad (23)$$

It is known that if $V_L/V_T>1.8$, this equation has one real root and two complex conjugate roots. The real root corresponds to the velocity $V_R$ of a propagative surface wave (Rayleigh wave). The complex roots correspond also to a physical surface wave termed as the leaky surface wave with propagation velocity $V_{LS}$. By using the relation $V_L \gg V_T$ in equation (23), it is found that:

$$V_R=0.96V_T; V_{LS}=(1.97\pm i0.57)V_T \quad (24)$$

Therefore, the Rayleigh velocity has a simple relation with the shear velocity: $V_R \cong 0.96V_T$. Thus, many authors use, as inversion algorithm to estimate $c_{44}$ from surface wave measurements, the following expression:

$$c_{44}=\rho(V_R/0.96)^2 \quad (25)$$

However, this relationship only holds in a semi-infinite medium and in the far-filed where the leaky wave is negligible due to its complex velocity. Real samples are, of course, finite. Thus, in order to meet the conditions for equation (25) to be valid, many authors employ high frequency wave propagation. In this way, the wavelength of the Rayleigh wave is much lesser than the sample's height and the medium is considered semi-infinite Nevertheless, the use of high frequencies is not desirable for many reasons. Firstly, because the surface wave only senses a small portion of the whole sample (its penetration depth is limited to one wavelength). In addition, real samples are attenuating. The attenuation coefficient grows as a power of frequency. Thus, the higher the frequency, the smaller the propagation distance of the wave. Finally, for high frequencies, the compressional wave is not negligible and guided wave propagation is not avoidable.

If the wavelength of the shear wave is comparable to the height of the sample being tested, the inversion algorithm used in equation (25) is no longer valid. In such case, many authors appeal to the Rayleigh-Lamb model of guided wave propagation in plates. Since low frequencies are employed, inversion algorithms based on the zeroth order modes are used because these are the only modes without a cutoff frequency. However, data is usually collected in the near-field of the source and for short times. Within these conditions, the Rayleigh-Lamb modes are not yet developed. This fact leads to biases in the estimation of $V_T$. Therefore, in the present invention, a different inversion algorithm is used to retrieve the shear wave velocity $V_T$ from surface displacements.

Figure 5:
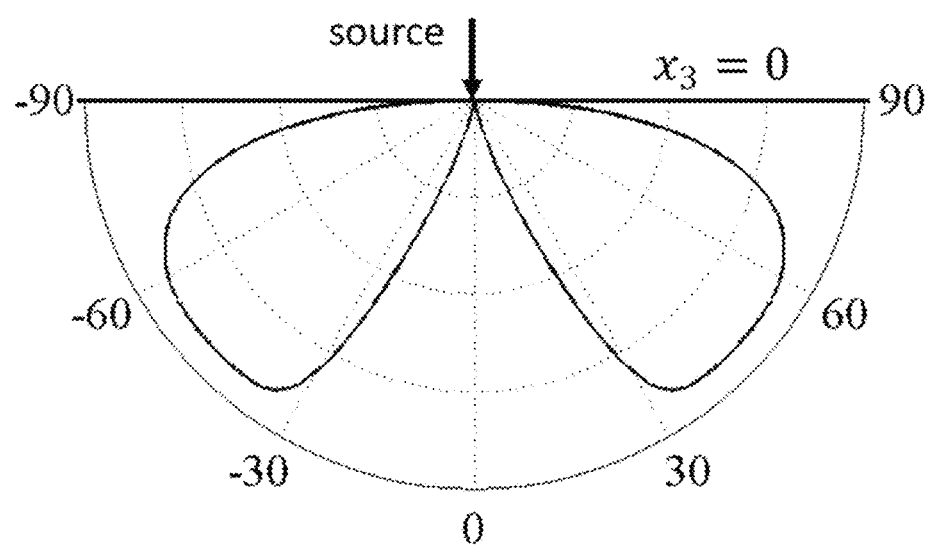
FIG. 5: Displays the directivity diagram of shear waves created by a rectangular head piece in a semi-infinite isotropic elastic solid. The maximum amplitude is attained at 34°. Below this angle, the amplitude decreases rapidly to 0.
Figure 6:
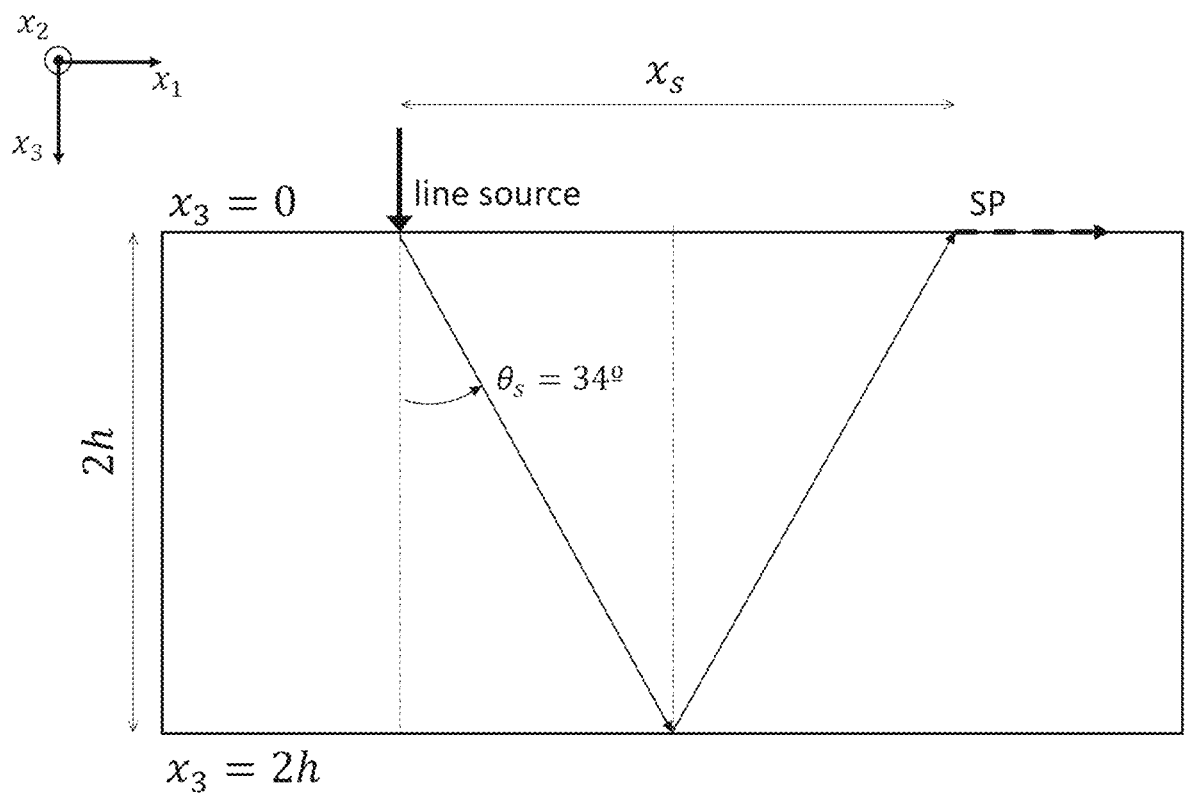
FIG. 6: is a schematic representation of bulk shear wave propagation within the solid and mode conversion to SP surface wave. The coordinate system is also displayed.

Consider a homogeneous soft-solid isotropic elastic plate of height 2h which is excited by a source located at the free surface in $x_3=0$ as displayed in FIG. 6. The source vibrates normally to the free surface of the plate, i.e. in the $x_3$ direction. If the vibration frequency is chosen appropriately, only shear waves propagate into the bulk of the plate as expressed in equation (13). The directivity diagram $H(\theta)$ of the shear wave for a source acting normally to the free surface is given by:

$$H(\theta) = \frac{\cos(\theta)\sin(2\theta)\left[\left(\frac{V_L}{V_T}\right)^2 \sin^2(\theta)-1\right]}{(2\sin^2(\theta)-1)^2 - 4\sin^2(\theta)\sqrt{\sin^2(\theta)-1}\sqrt{\sin^2(\theta)-\left(\frac{V_T}{V_L}\right)^2}} \quad (26)$$

and displayed in FIG. 5. The angle for the maximum value in the lobe is 34° with respect to the source's axis. The displacement amplitude of the wave decreases rapidly for angles below 34°. Thus, only waves propagating above this direction will produce appreciable reflected waves. This wave reaches the opposite surface at $x_3=2h$ and reflects back into the medium with the same angle. It reaches the free surface $x_3=0$ at a distance $x_s$ from the source given by: $x_s=4h \tan 34° \cong 2.7h$. Since the compressional wave is negligible, the surface displacement field at $x_3=0$ and $0<x_1<x_s$ has not contributions from the opposite surface. Thus, within this region only surface waves propagate. This include the Rayleigh wave but also the leaky surface wave. The leaky surface wave attenuates as it propagates along the $x_1$ direction. Using the values of $V_{LS}$ from equation (24), it is found that its phase velocity is twice the shear wave velocity and its characteristic attenuation distance is given by:

$$\zeta = \frac{1}{\text{Im}\left[\frac{\omega}{V_{LS}}\right]} \cong 1.1\lambda_T \quad (27)$$

where $\lambda_T$ is the shear wavelength. Thus, the attenuation distance of the leaky surface wave along the x direction is comparable to the shear wavelength in soft-solids. Therefore, the inversion algorithm expressed in equation (25) is valid only if $\zeta \ll x_1 < x_s$. However, the value of is not negligible at low frequencies. For example, typical values of the involved velocities in soft-tissues are $V_L \sim 1500$ m/s and $V_T \sim 10$ m/s. Therefore, the shear wavelength may vary from 10 to 1 cm for excitation frequencies in the range 100-1000 Hz. Then, the leaky wave is not negligible in the near-field. Therefore, interference between the Rayleigh and the leaky surface wave is possible. This fact has consequences over the phase velocity of the surface field as shown below.

Note that, depending on frequency, the value of can be greater than $x_s$. A critical frequency $f_c$ can be defined such as $\zeta = x_s$. The value of $f_c$ is given by:

$$1.1 \frac{V_T}{f_c} = 2.7\, h \Rightarrow f_c = 0.4 \frac{V_T}{h} \qquad 28$$

From the considerations above, the $x_3$-component of the surface displacement $u_3$ ($x_1 < x_s$, $x_3 = 0$) for frequencies below $f_c$ can be written as:

$$u_3(x_1 < x_s) = \exp(-ik_R x_1) - \exp(-x_1/\zeta)\exp(-ik_{LS} x_1) \qquad 29$$

corresponding to the sum of the Rayleigh and leaky surface wave, where $k_{LS}$ is the real part of the wavenumber of the leaky surface wave. For low frequencies, $k_R x_1 \ll 1$ and therefore:

$$u_3(x_1 < x_s) \cong \left[ 1 - \exp(-x_1/\zeta) + \frac{k_R^2}{2}(\delta^2 \exp(-x_1/\zeta) - 1) x_1^2 \right] + \\ ik_R \left[ (1 - \delta \exp(-x_1/\zeta)) x_1 + \left( \frac{\delta^3 \exp(-x_1/\zeta) - 1}{6} \right) k_R^2 x_1^3 \right] \qquad 30$$

where $\delta$ is defined as $\delta = k_{LS}/k_R \cong \tfrac{1}{2}$. Defining $$N(x_1, \omega, V_T) = k_R\left[(1 - \delta \exp(-x_1/\zeta))x_1 + \left(\frac{\delta^3 \exp(-x_1/\zeta) - 1}{6}\right) k_R^2 x_1^3\right], \text{ and}$$

$$D(x_1, \omega, V_T) = 1 - \exp(-x_1/\zeta) + \frac{k_R^2}{2}(\delta^2 \exp(-x_1/\zeta) - 1) x_1^2,$$

the phase $\phi(x_1, \omega, V_T)$ of this wave can be expressed as:

$$\phi(x_1, \omega, V_T) = \operatorname{atan}\!\left(\frac{N(x_1, \omega, V_T)}{D(x_1, \omega, V_T)}\right) \qquad 31$$

Thus, the phase velocity V of the surface wave for a given frequency $\omega_0$ is expressed as:

$$V(x_1, \omega_0, V_T) = \omega_0 \left(\frac{\partial \phi}{\partial x_1}\right)^{-1} = \\ \omega_0 \left( \frac{D^2(x_1, \omega_0, V_T) + N^2(x_1, \omega_0, V_T)}{N'(x_1, \omega_0, V_T) D(x_1, \omega_0, V_T) - N(x_1, \omega_0, V_T) D'(x_1, \omega_0, V_T)} \right) \qquad 32$$

where the primes over the function indicates derivative with respect to $x_1$. Note that this expression gives a different dispersion curve for each value of $x_1$. Thus, it is not the dispersion curve for Rayleigh-Lamb modes. At this stage, two inversion methods are envisaged to retrieve $V_T$ from the experimental values of V.

First inversion method. If, for a given position $x_1 < x_s$, an experimental dispersion curve $V(\omega)$ for frequencies $\omega > \omega_c = 2\pi f_c$ is available, then equation (32) can be fitted in a least-squares sense to the experimental data. The value of $V_T$ that minimizes the sum of quadratic differences is the best estimation for the shear wave velocity. This was the inversion method employed in FIG. 7.

Second inversion method. If, for a given position $x_1 < x_s$, a single value of V is available, corresponding to a single frequency $\omega_0 > \omega_c$, then equation (32) can be used to build the curve $V(V_T)$. The abscissa corresponding to the intersection between the experimental and theoretical values gives the estimation for the shear wave velocity $V_T$.

So far, the inversion methods proposed above only consider the surface displacement field for $x_1 < x_s$. If $x_1 > x_s$, the reflected shear waves are not negligible and must be taken into account in the inversion method. To this end, the effects of an impinging shear wave on the free surface must be considered first.

Consider an impinging shear wave at the free surface $x_3 = 0$. This wave produces a reflected shear wave and, due to mode conversion, a reflected compressional wave. If $A_s^i$ and $\theta_s^i$ are the amplitude and angle of the incident shear wave, the amplitude $A_p^r$ and angle $\theta_p^r$ of the reflected compressional wave are given by:

$$\sin(\theta_p^r) = \frac{V_L}{V_T}\sin(\theta_s^i) \qquad 33$$

$$A_p^r = -\frac{2(V_L/V_T)^2 \sin(2\theta_s^i)\cos(2\theta_s^i)}{\sin(2\theta_p^r)\sin(2\theta_s^i) + (V_L/V_T)^2 \cos^2(2\theta_s^i)} A_s^i \qquad 34$$

Since $V_L \gg V_T$, the angle of is complex even if $\theta_s^i \ll 1$. Let $\theta_r^p = \pi/2 - i\gamma$ where $\gamma$ is real and positive. Consider now the components of the wavevector $\vec{k}^p$ of the reflected compressional wave along $x_1$ and $x_3$:

$$k_1^p = k^p \sin(\theta_p^r) = k^p \sin(\pi/2 - i\gamma) = k^p \cos h(\gamma)$$

$$k_3^p = k^p \cos(\theta_p^r) = k^p \cos(\pi/2 - i\gamma) = i k^p \sin h(\gamma)$$

Thus, whatever the incident angle, the impinging shear wave produces an evanescent compressional wave confined to the free surface of the soft-solid. Thus, it is a surface wave which we call the SP wave (FIG. 6). The phase velocity $V_{SP}$ of this wave along the $x_1$-direction can be computed as:

$$V_{SP} = \frac{\omega}{k_1^p} = \frac{V_T}{\sin(\theta_s^i)}$$

Therefore, the phase velocity of the SP wave varies from nearly infinite for $\theta_s^i \cong 0$ to $V_T$ for $\theta_s^i \cong \pi/2$. After some computation, the amplitude of the SP wave is given by:

$$A_p^r \cong -\frac{2\,\sin(2\theta_s^i)\cos(2\theta_s^i)}{2i\,\sin^2(\theta_s^i)\sin(2\theta_s^i) + \cos^2(\theta_s^i)} A_s^i$$

where the approximation is valid if $\gamma \gg 1$. This is always the case since $\theta_s^i \geq 34°$. Thus, due to the complex denominator, the SP wave is out of phase with the reflected shear wave. The phase difference depends upon the incident angle $\theta_s^i$ of the shear wave. We expect to observe the SP wave whenever the amplitude $A_s^i$ of the shear wave is maximum. According to the directivity pattern of the shear wave, it has a maximum for $\theta_s^i \cong 34°$. At this angle, the phase velocity of the SP wave is $V_{SP} \cong 1.8 V_T$. Thus, the surface displacement field in the vicinity of $x_s$ is a complicated superposition of different wave types, each with its own phase velocity. If $\omega > \omega_c$ the $x_3$ component of the surface field can be expressed as the superposition of the Rayleigh wave, the reflected shear wave and the SP wave as:

$$u_3(x_1 \approx x_s) = e^{-ik_R x_1} + A_s(x_1)[e^{-ik_s^1 x_1} + |A_r^P(\theta_s)|e^{-i(k_{sp} x_1 + \eta)}] \quad 35$$

where $k_s^1$ is the component of the shear wave vector along $x_1$, $\eta$ is the phase angle of the SP wave with respect to the shear wave and $A_s(x_1)$ is the amplitude of the reflected shear wave at $\theta \cong \theta_s = 34°$. Taking into account the directivity and the geometrical attenuation, it is given by:

$$As(x_1) = \frac{H(\theta_s)}{(x_1^2 + 16h^2)^{1/2}}$$

Now, for low frequencies, equation (35) can be expressed as:

$$u_3(x_1 \approx x_s) \cong 1 + A_s(x_1)|A_r^P(\theta_s)|(\cos(\eta) - k_{sp} \sin(\eta)) - \\
\frac{1}{2}((k_R^2 + A_s(x)(k_s^1)^2 + A_s(x_1)|A_r^P(\theta_s)|k_{sp}^2 \cos(\eta))) \\
x_1^2 + \frac{1}{6}A_s(x_1)|A_r^P(\theta_s)|k_{sp}^2 \sin(\eta)x_1^3 - i[A_s(x_1)|A_r^P \\
(\theta_s)|\sin(\eta) + (k_R + A_s(x_1)|A_r^P(\theta_s)|k_{sp} \cos(\eta) + A_s(x) \\
k_s^1)x_1 - \frac{1}{2}A_s(x_1)|A_r^P(\theta_s)|k_{sp}^2 \sin(\eta)x_1^2 - \frac{1}{6}(k_R^3 + \\
A_s(x_1)(k_s^1)^3 + A_s(x_1)|A_r^P(\theta_s)|k_{sp}^3 \cos(\eta))x_1^3] \quad 36$$

Defining $N_s(x) = \text{Im}[u_z]$ and $D_s(x) = \text{Re}[u_z]$, the phase velocity is expressed as:

$$V(x_1 \approx x_s, \omega_0, V_T) = \omega_0 \left( \left( \frac{D_s^2(x_1, \omega_0, V_T) + N_s^2(x_1, \omega_0, V_T)}{N_s'(x_1, \omega_0, V_T) D_s(x_1, \omega_0, V_T) - N_s(x_1, \omega_0, V_T) D_s'(x_1, \omega_0, V_T)} \right) \right) \quad 37$$

Thus, a third inversion method is possible:

Third inversion method. If, for a given position $x_1 \approx x_s$, an experimental dispersion curve $V(\omega)$ for frequencies $\omega > \omega_c$ is available, then equation (37) can be fitted in a least-squares sense to the experimental data. The value of $V_T$ that minimizes the sum of quadratic differences is the best estimation for the shear wave velocity. This was the inversion method employed in FIG. 8.

A third possibility regarding the position $x_1$ at which the surface displacement is measured must be considered. If $x_1 \gg x_s$ a few reflections back and forth in the interfaces of the sample have taken place. Thus, in this zone, the Rayleigh-Lamb modes have developed. Due to the source type and polarization used in this invention, it favors the antisymmetric modes. In addition, since low-frequencies are employed, only the zeroth order mode propagate. Thus, other two inversion methods are possible, in the same spirit of methods #1 and #2:

Fourth inversion method. If, for a given position $x_1 \gg x_s$, an experimental dispersion curve $V(\omega)$ is available, then the zeroth order antisymmetric Rayleigh-Lamb mode can be fitted in a least-squares sense to the experimental data. The value of $V_T$ that minimizes the sum of quadratic differences is the best estimation for the shear wave velocity. This was the inversion method employed in FIG. 9.

Fifth inversion method. If, for a given position $x_1 \gg x_s$, a single value of V is available, corresponding to a single frequency $\omega_0$, then the zeroth order antisymmetric Rayleigh-Lamb mode can be used to build the curve $V(V_T)$. The abscissa corresponding to the intersection between the experimental and theoretical values gives the estimation for the shear wave velocity $V_T$.

As a final observation for isotropic solids, we note here that, due to the interference of the different surface wave types, the amplitude of the surface displacement is a complicated function of position x and frequency $\omega$. Thus, an estimation of the attenuation coefficient by fitting the amplitude of the displacement field to the usual exponential decay does not make sense, at least in the near field. If far-field $(x_1 \gg x_s)$ measurements are available, then, the amplitude should be corrected by diffraction before trying to estimate the attenuation coefficient.

Transversely Isotropic Solid

Potential applications of the present invention include estimating the elastic properties of skeletal semi-tendinous muscles, e.g., meat samples or application in vivo to external human muscles such as biceps, triceps, quadriceps, etc. Due to the parallel fiber orientation in these kind of muscles, they can be modelled as transversely isotropic materials. In addition, some long-chain polymers with chains aligned within a preferred direction are also modelled as transversely isotropic materials.

Figure 4:
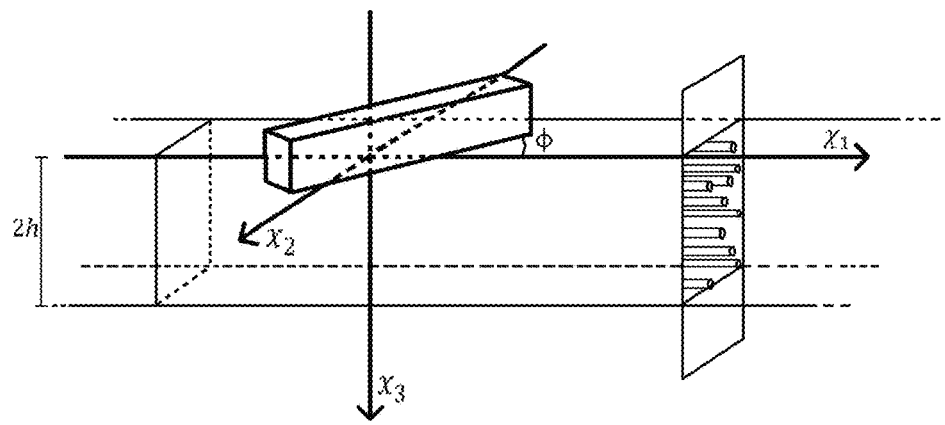
FIG. 4: shows the coordinate system orientation for the transversely isotropic solid. The symmetry axis is oriented along the $x_1$ direction parallel to the fibers (either, muscle fibers or long molecule chains). The rectangular head piece oriented with an angle $\phi$ with respect to the $x_1$ direction is also displayed.

The stiffness matrix has five independent elastic modulus for this kind of materials. Let $x_1$ be the axis of symmetry, i.e., the orientation axis of muscular fibers or long molecule-chains. Thus, the axes $x_2$ and $x_3$ are perpendicular to the fibers as shown in FIG. 4. For this choice of axes orientation, the stiffness matrix reads:

$$C_{\alpha\beta} = \begin{pmatrix} c_{11} & c_{12} & c_{12} & 0 & 0 & 0 \\ c_{12} & c_{22} & c_{22} - 2c_{44} & 0 & 0 & 0 \\ c_{12} & c_{22} - 2c_{44} & c_{22} & 0 & 0 & 0 \\ 0 & 0 & 0 & c_{44} & 0 & 0 \\ 0 & 0 & 0 & 0 & c_{55} & 0 \\ 0 & 0 & 0 & 0 & 0 & c_{55} \end{pmatrix} \quad 38$$

The constants $c_{11}$ and $c_{22}$ are related to the compressional wave propagating along and perpendicular to the symmetry axis respectively: $V_L^{\parallel} = \sqrt{c_{11}/\rho}$ and $V_L^{\perp} = \sqrt{c_{22}/\rho}$. In many incompressible transversely isotropic solids (such as skeletal muscle for example), these two values of compressional wave velocities are almost equal each other. Thus, $c_{22} \cong c_{11}$, i.e. the solid is isotropic regarding the compressional waves. The constant $c_{44}$ is related to a shear wave propagating perpendicular to the symmetry axis with perpendicular polarization $V_T^{\perp} = \sqrt{c_{44}/\rho}$. The constant $c_{55}$ is related to a shear wave propagating parallel to the symmetry axis with perpendicular polarization $V_T^{\perp} = \sqrt{c_{55}/\rho}$. As in the isotropic solid case, $V_L \gg V_T$, whatever the polarization. Thus, $c_{22} - 2c_{44} \cong c_{22} \cong c_{11}$. Finally, the constant $c_{12}$ is related to wave propagation (either compressional or shear waves) in directions out of the principal axes.

Consider now an anisotropic soft-solid where $V_L \gg V_T$ whatever the propagation direction of the waves. The wave equation for this case cannot be written in a simple manner as for the isotropic case. However, it is still valid that the contribution of the compressional waves are negligible at low-frequencies. Thus, low-frequency waves propagate almost as shear waves. The objective of the present invention, when applied to transversely isotropic solids, is to estimate either $c_{44}$, $c_{55}$ or both of them.

A. Estimation of $c_{44}$

If wave propagation takes place in a plane perpendicular to the symmetry axis (plane $(x_2, x_3)$ in FIG. 4), the shear wave velocity is $V_T^{\perp}$ and is independent of the propagation direction within this plane. Using the aforementioned relations between elastic constants for the soft solid case, i.e., $c_{22} = c_{11}$ and $c_{22} - 2c_{44} = c_{11}$, the Rayleigh wave equation takes exactly the same form as in the isotropic case with $V_L = \sqrt{c_{11}/\rho}$ and $V_T^\perp = \sqrt{c_{44}/\rho}$. Therefore, if the source does not excite the $u_1$ component of the field, the inversion method to estimate $c_{44}$ proceeds exactly as for the isotropic soft-solid. To achieve this condition, the invention is equipped with a line source (item(1), FIG. 3). The length of the line source is much longer than the shear wavelength (i.e. the line source is "infinite"). If the source is aligned parallel to the $x_1$ direction, it excites the $u_2$ and $u_3$ components of the field, but not the $u_1$ component.

B. Estimation of $c_{55}$

For estimating $c_{55}$, consider the line source oriented parallel to the $x_2$ axis. For this case, the wave propagation takes place in a plane that includes the symmetry axis (plane $(x_1, x_3)$ in FIG. 4). The secular equation for the Rayleigh wave under this condition is given by:

$$(\partial - \rho V^2)\sqrt{1 - \frac{\rho V^2}{c_{55}}} - \rho V^2 = 0 \qquad 39$$

where $\partial = c_{11} + c_{22} - 2c_{12}$. Since the medium is considered isotropic for compressional waves, the constant $c_{12}$ is no longer an independent constant. It is related to other constants by:

$$c_{12} = c_{11} - c_{55}$$

Since $c_{22} = c_{11}$, the secular equation (39) is expressed as:

$$\left(2 - \left(\frac{V}{V_T^{||}}\right)^2\right)\sqrt{1 - \left(\frac{V}{V_T^{||}}\right)^2} - \left(\frac{V}{V_T^{||}}\right)^2 = 0 \qquad 40$$

As for the isotropic case, this equation has one real root (corresponding to the Rayleigh wave) and two complex conjugate roots corresponding to the leaky surface wave:

$$V_R = 0.84 V_T^{||}; V_{LS} = (1.42 \pm 0.6i) V_T^{||} \qquad 41$$

Note that the attenuation distance for the leaky wave $\zeta$ is larger than for the isotropic case, $\zeta = 1.6 \lambda_T$. Another difference with respect to the isotropic solid concerns the directivity pattern of the shear wave. There is no simple expression for the directivity pattern in the $(x_1, x_3)$ plane. However, some authors have computed it numerically. It is shown that the main lobe is oriented towards 60° from the source. Therefore the value of $x_s$ is now given by $x_s \cong 7h$. Thus, the value of the critical frequency at which $\zeta = x_s$ is given by $f_c = 0.23 V_T/h$, which is lower than the isotropic case. Therefore, if $x_1 < x_s$ and $\omega > \omega_c = 2\pi f_c$, the inversion method to obtain $c_{55}$ proceeds as given by equation (32) for the isotropic solid but changing the values of $V_R$ and $V_{LS}$ by the ones given in equation (41).

Inversion procedures for $x_1 \geq x_s$ are complicated since no analytic expressions are available for the directivity of shear waves. In addition, Rayleigh-Lamb modes in the $(x_1, x_3)$ plane are difficult to compute even numerically. Therefore, the present invention does not include inversion methods for these cases.

The lack of inversion algorithm for $x_1 > x_s$, does not forbids the estimation of $c_{55}$ in common applications of the invention. Consider for example skeletal muscles such as biceps branchii. The mean value of its height in adults is $2h = 28 \pm 7$ mm. Thus, $x_s \cong 7h \cong 100$ mm. The mean height for other skeletal muscles like vastus lateralis or vastus medialis is even larger than 28 mm. Therefore, if the data is collected at positions $x < 100$ mm, the value of $c_{55}$ can be estimated by the inversion methods proposed in the present invention.

Application Examples

Temperature Dependence of $c_{55}$

Figure 11A:
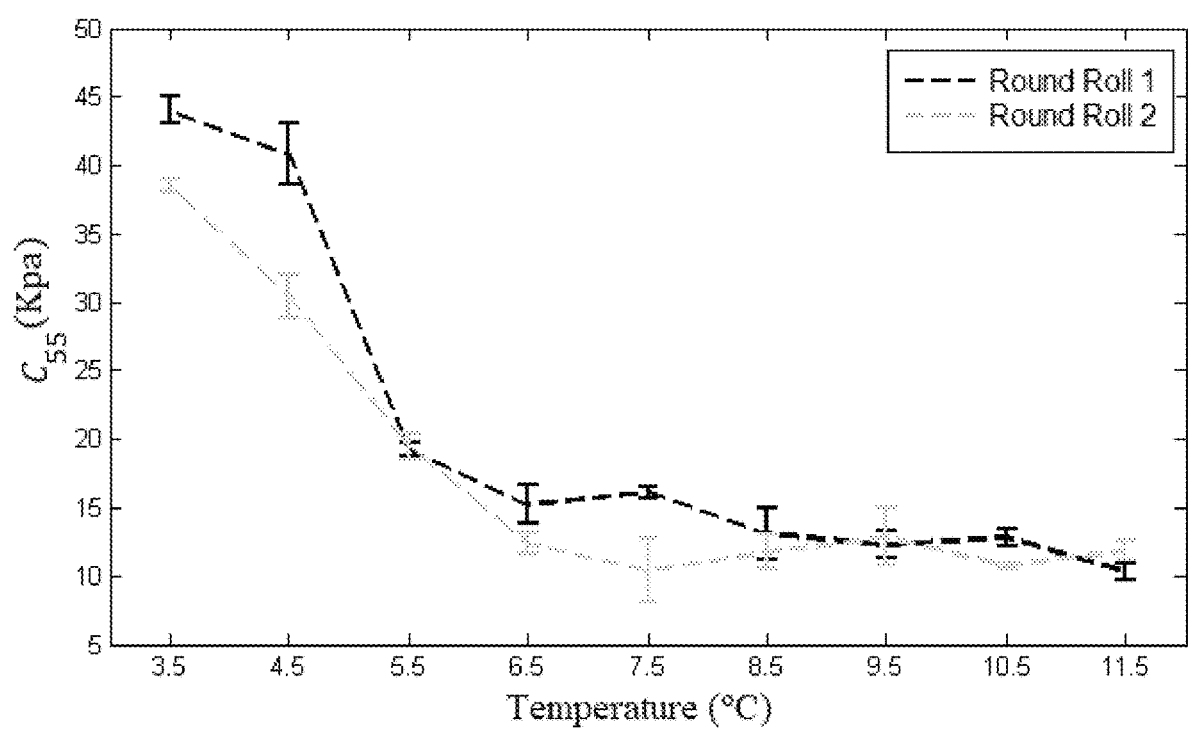
FIG. 11A-11B: displays an example of experimental data showing the dependence of $c_{55}$ with temperature in beef samples.
Figure 11B:
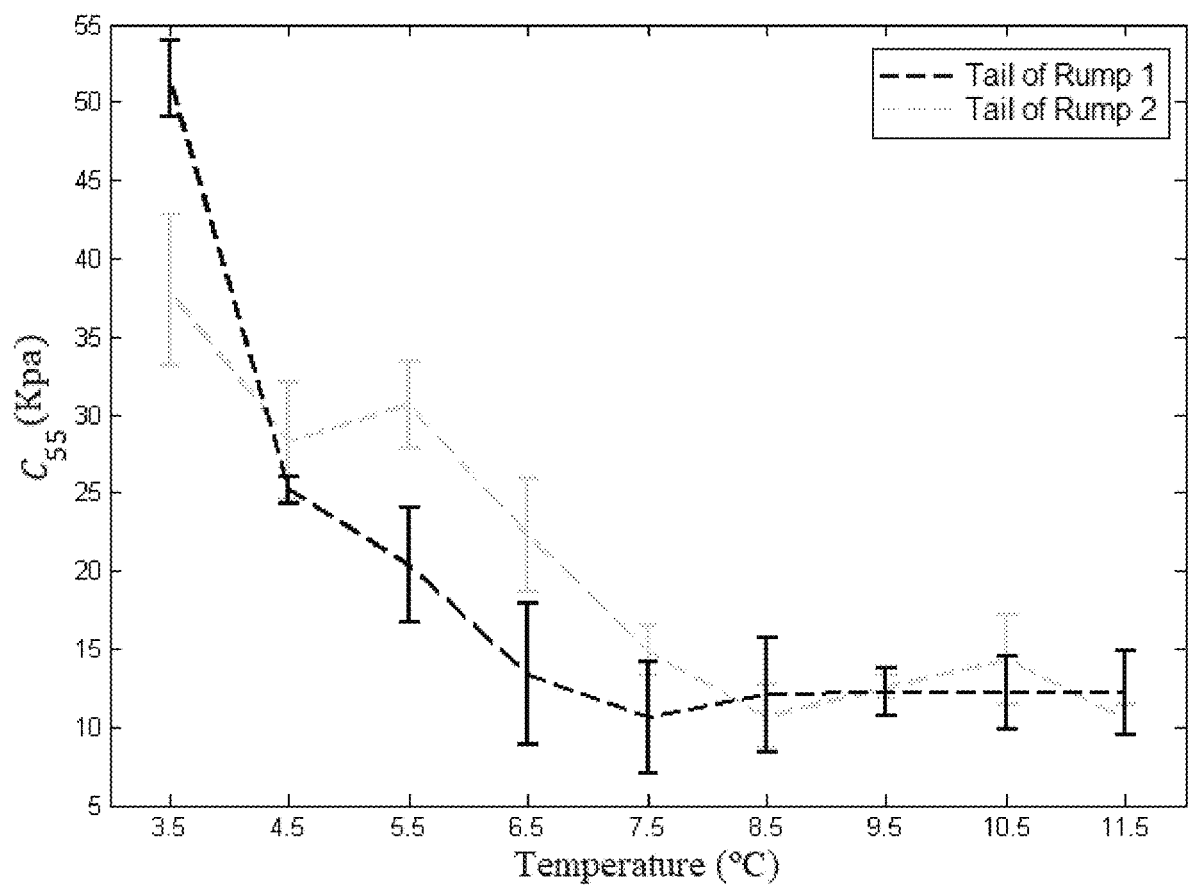
Figure 12A:
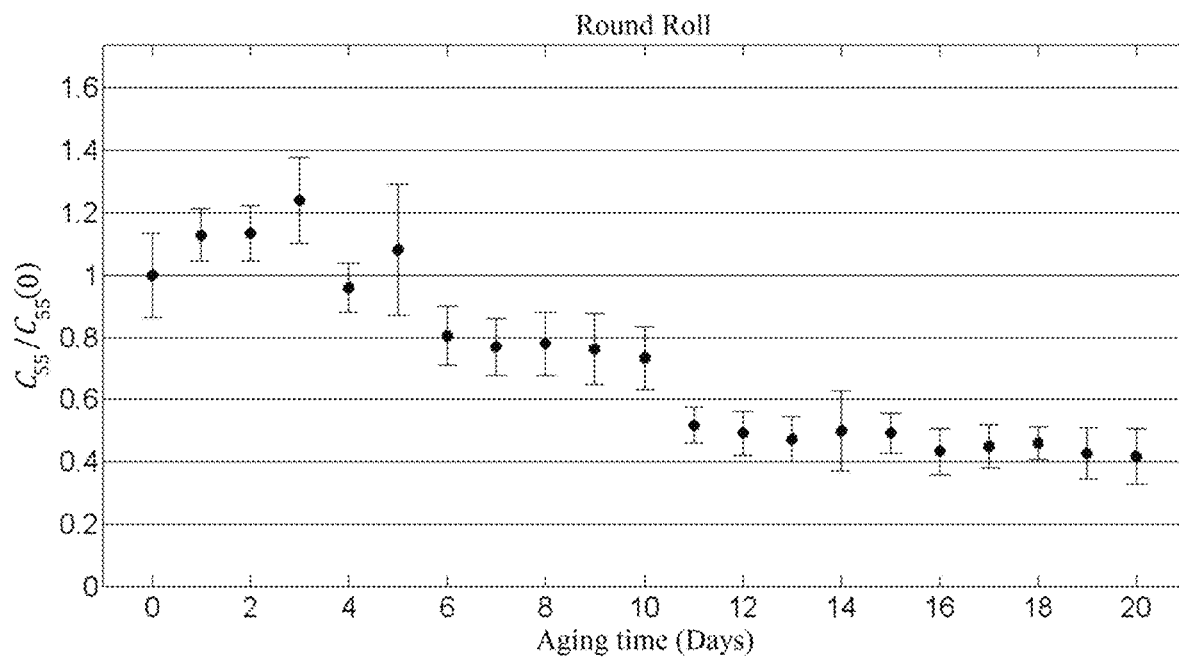
FIG. 12A-12E shows the relative elastic changes during age maturation process in different beef samples. All curves were normalized with respect to the value of $c_{55}$ at the first measurement. The errorbars represent one standard deviation over 10 measurements.
Figure 12B:
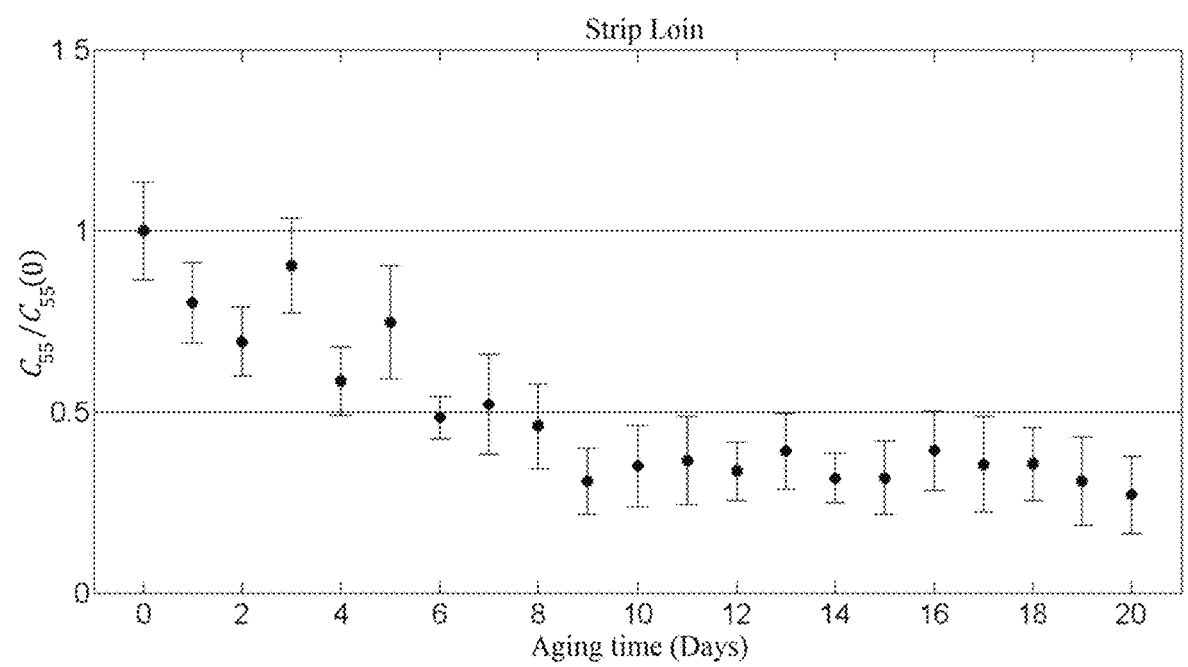
Figure 12C:
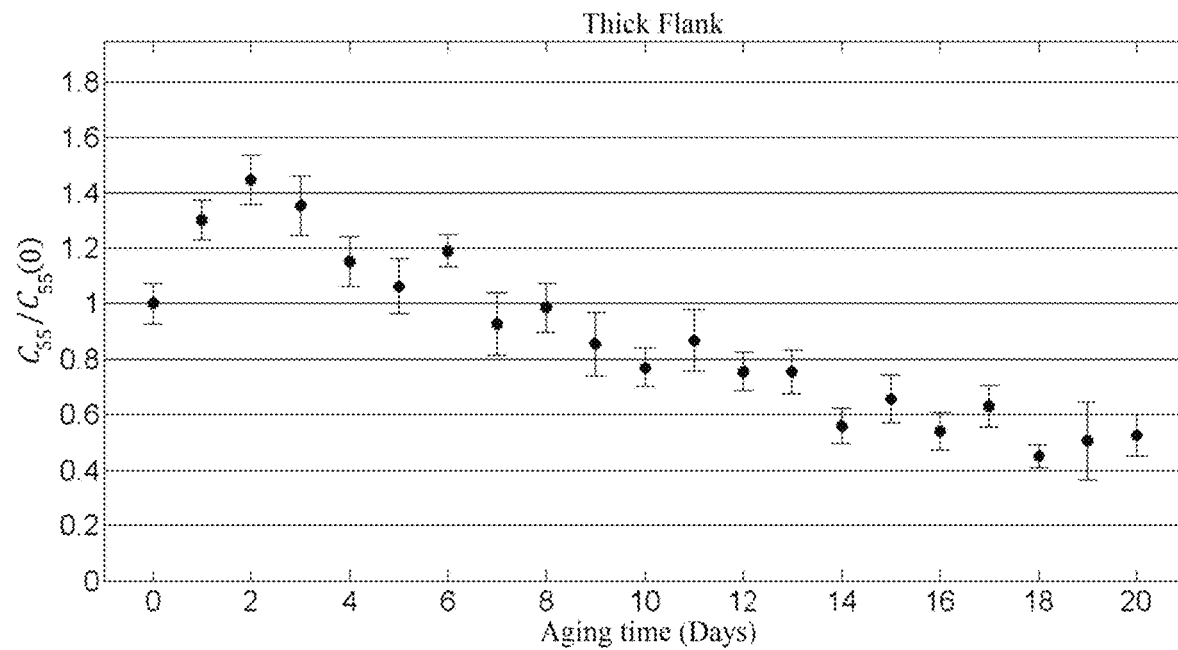
Figure 12D:
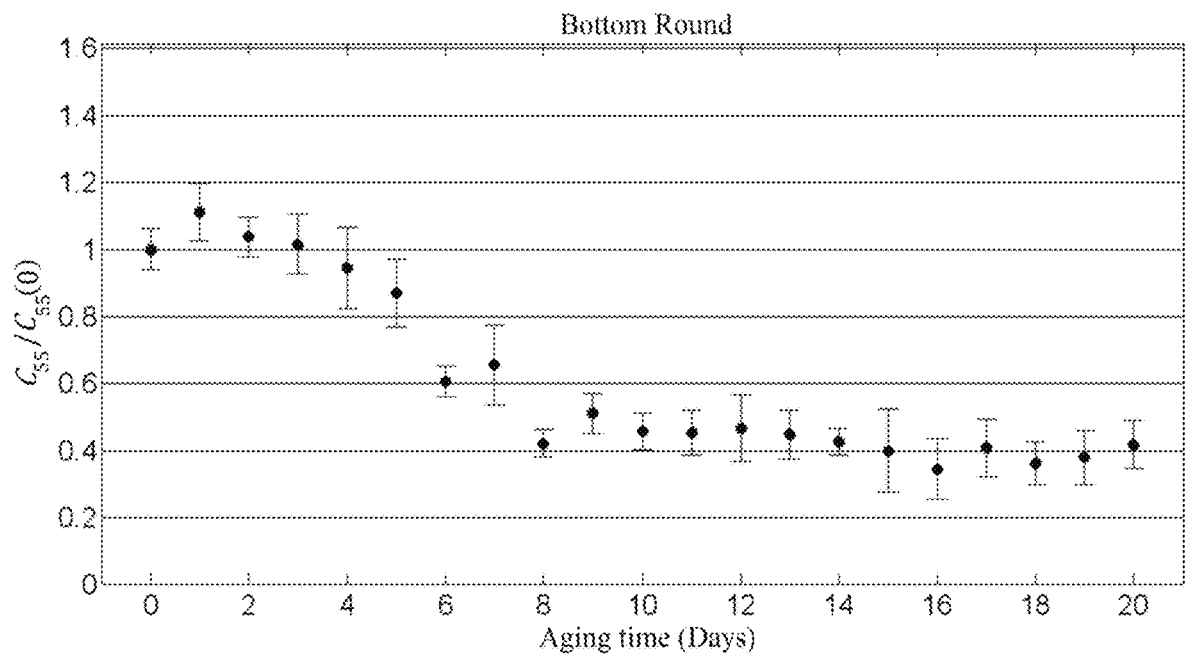
Figure 12E:
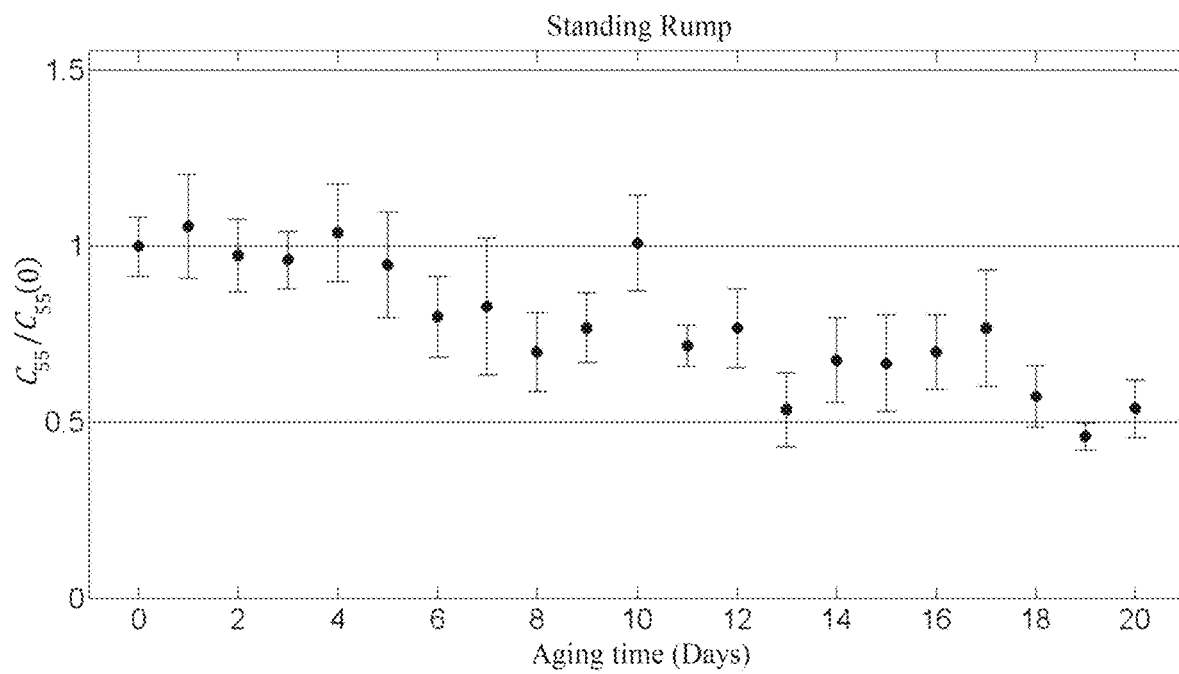

The elasticity of soft tissues depends on the temperature. In order to compare the elasticity of different beef samples it is important that all are taken at the same temperature. However, this is not always the case. The temperature in slaughter houses can vary within a range between 3 and 10° C. In this example, the temperature dependence of $c_{55}$ in beef samples is shown in FIGS. 11A-11B. A consisted decrease in elasticity with temperature rise is observed in the samples tested.

Age Maturation Process

Age maturation is a fundamental process in meat industry. It is mediated by the action of many enzymatic systems. After rigor mortis, these enzymatic systems produce a progressive softening of beef allowing to reach the desired tenderness requested by consumers. There is a lack of nondestructive monitoring method of enzymatic maturation. In this example, the maturation process of 5 different cuts, consisting in 5 samples of each, is monitored with the present invention. The samples were kept vacuum sealed inside a cold room between 0 and 4° C. during 21 days. All samples were measured once a day. FIGS. 12A to 12E display the normalized elasticity with respect to the first day for each cut. The errorbars represent one standard deviation of the 5 samples for each cut. After initial fluctuations, a decrease in elasticity is observed for all samples. Roughly, an asymptotic value is reached around 14 days of maturation for all samples.

Comparison with Warner-Bratzler Shear Force Test (WBSF)

Figure 13A:
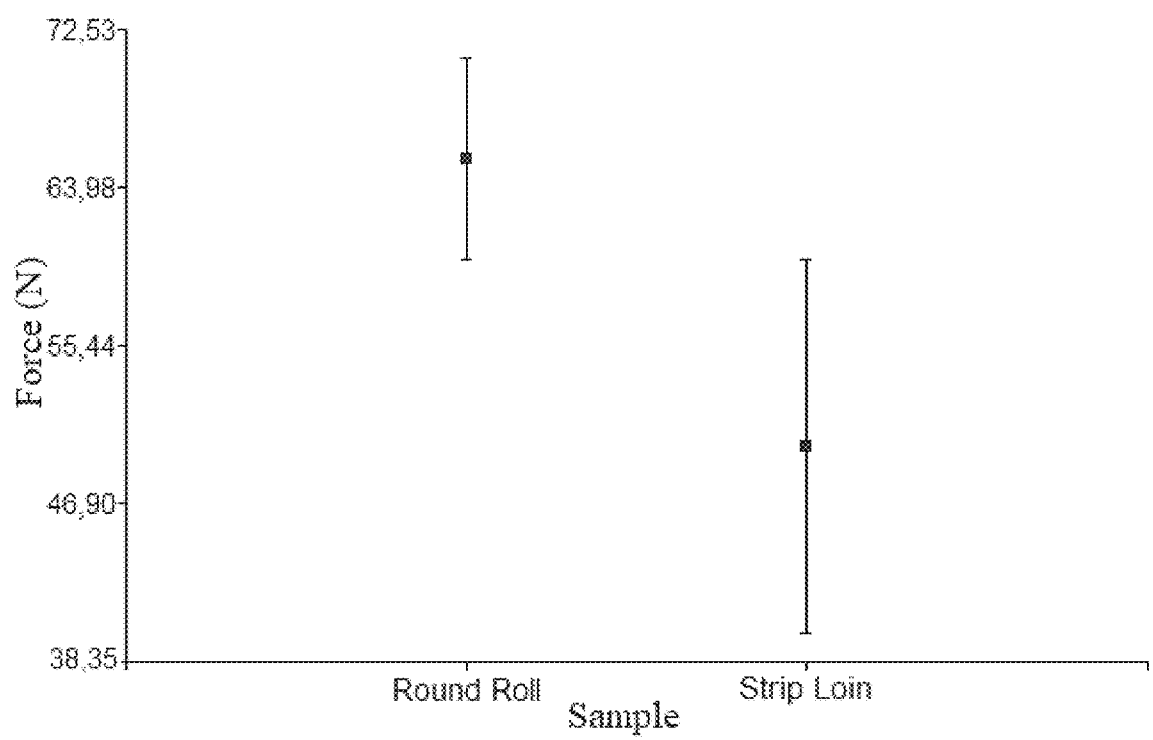
FIG. 13A-13C show a comparison of the performance of the present invention with results obtained by a standard Warner-Bratzler shear force (WBSF) test.
Figure 13B:
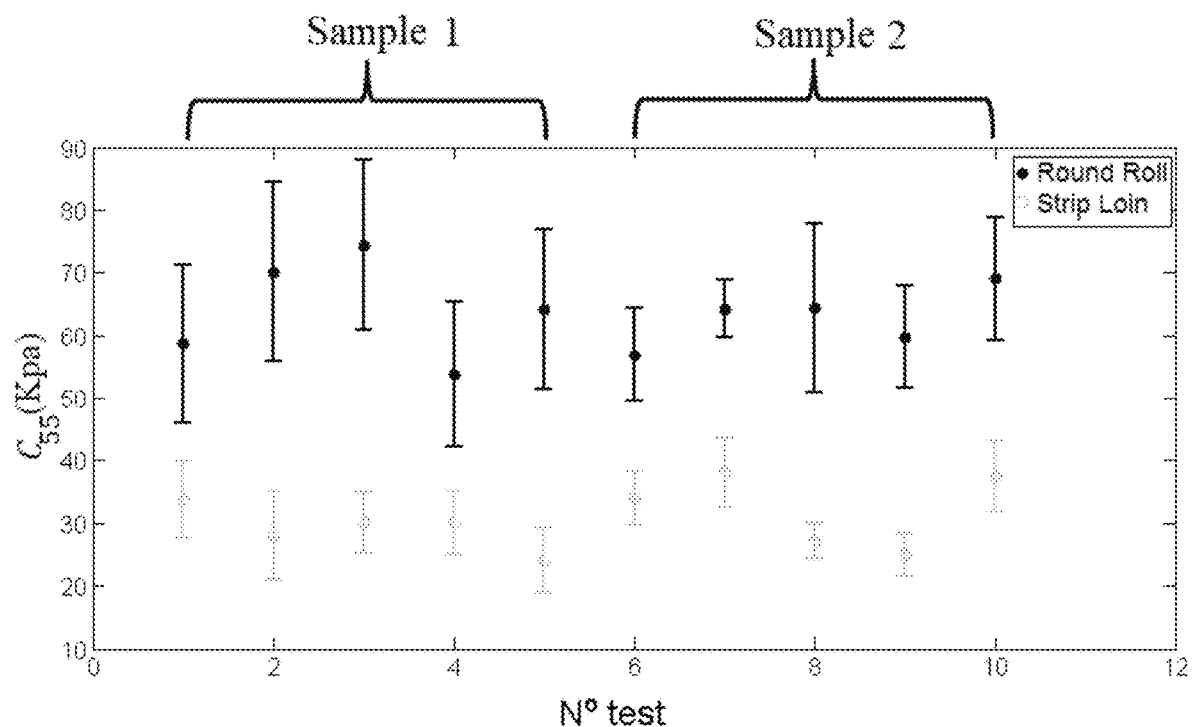
Figure 13C:
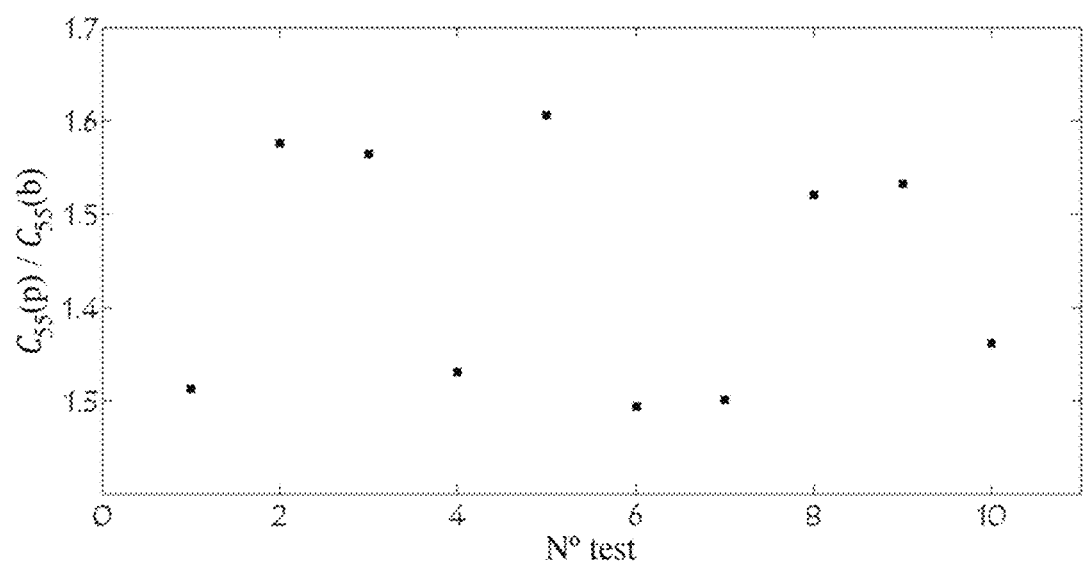

The WBSF test is a destructive method. It measures the force that a sharp inverted "V" shaped knife needs to cut the beef sample while moving at constant speed. It is the standard test in meat industry to quantify the tenderness. In this example, the results of WBSF tests in two different beef samples are shown (FIG. 13A). The results of the present invention applied to the same samples are shown in FIG. 13B. FIG. 13C displays the ratio between the elastic modulus of the two samples. This ratio is in agreement with the ratio expected from the WBSF tests (FIG. 13A)

Sorting Beef Cuts According to Tenderness

Figure 14:
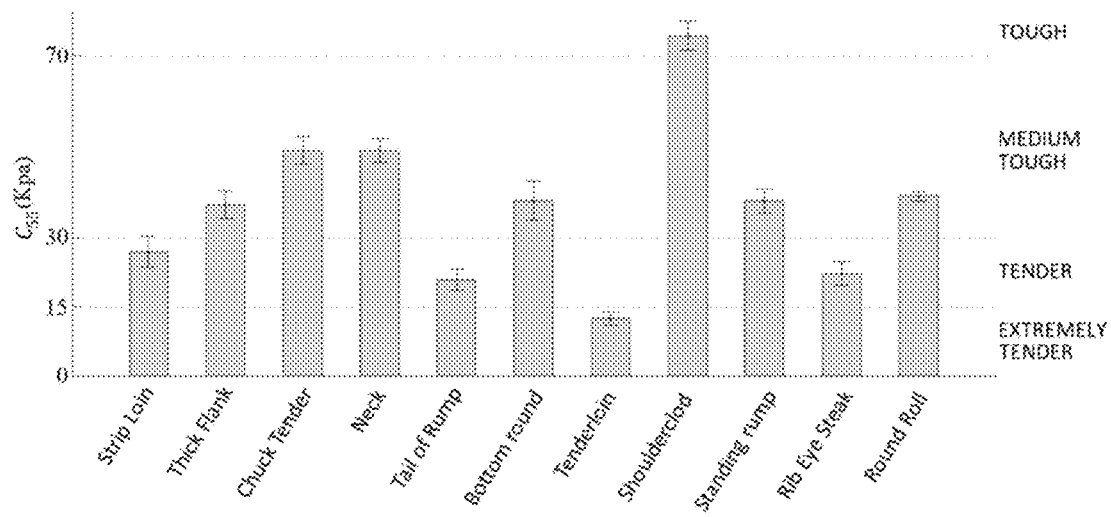
FIG. 14 displays an example of using the present invention to rate different beef cuts according to their elasticity value.

The tenderness of beef samples represents a variable that defines, in a high percentage, its commercial value. The standard procedure to evaluate tenderness is the WBSF test. In the previous example, it was shown that the shear force test and the elasticity are correlated. Thus, the present invention can be employed to discriminate beef samples according to their tenderness. FIG. 14 displays the elasticity value of different beef cuts and their classification according to 4 grades of tenderness: tough, medium tough, tender and extremely tender.

Elasticity Estimation in Skeletal Muscle in Vivo

Figure 15A:
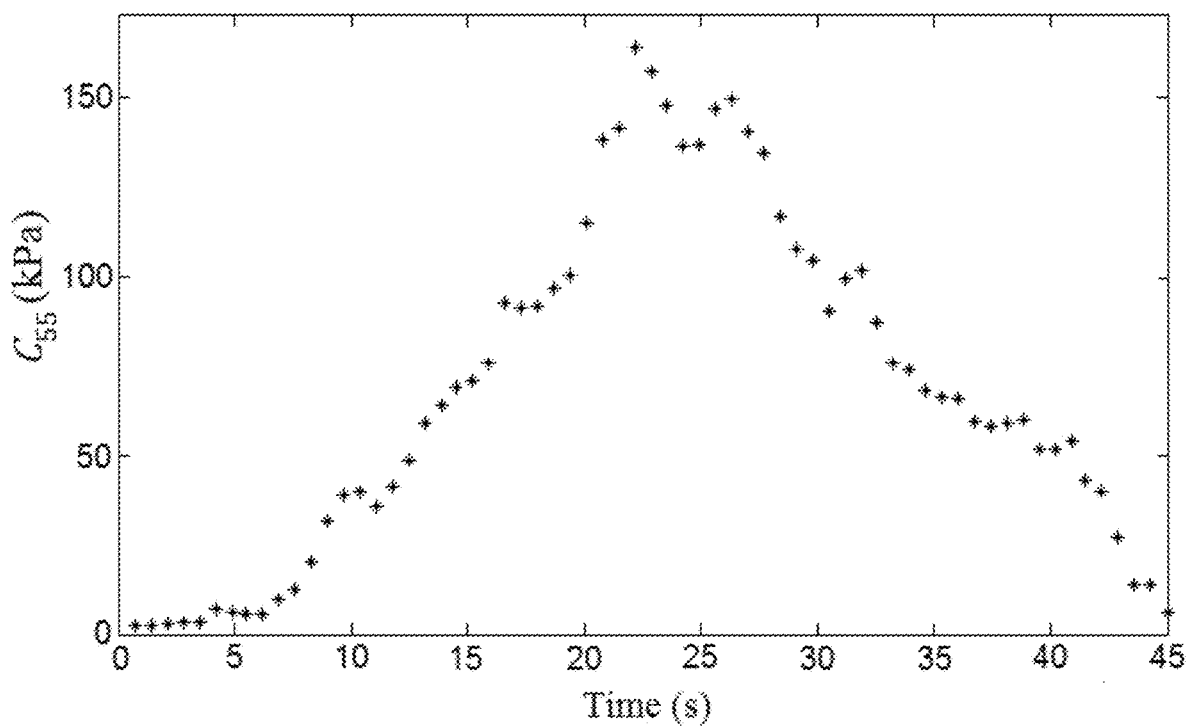
FIG. 15A-15C show examples of using the present invention to monitor the elasticity of skeletal muscle in vivo in dynamic situations.
Figure 15B:
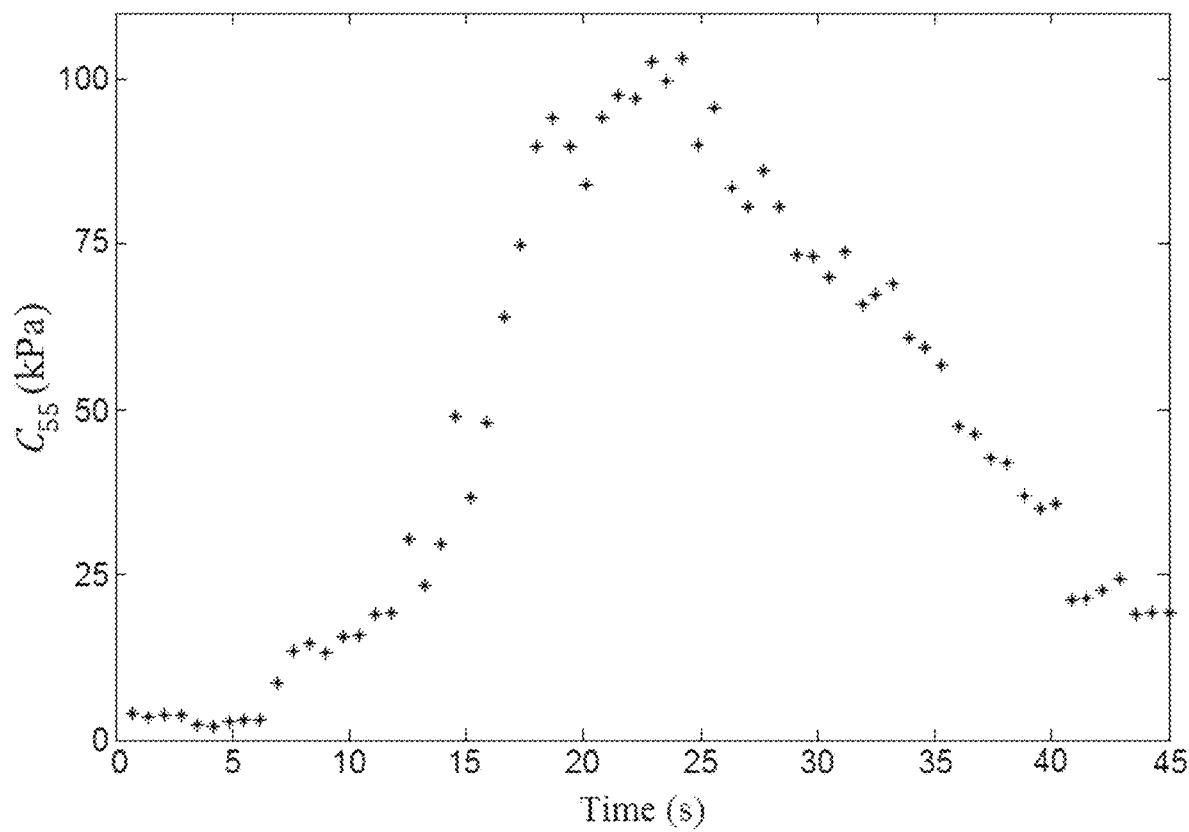
Figure 15C:
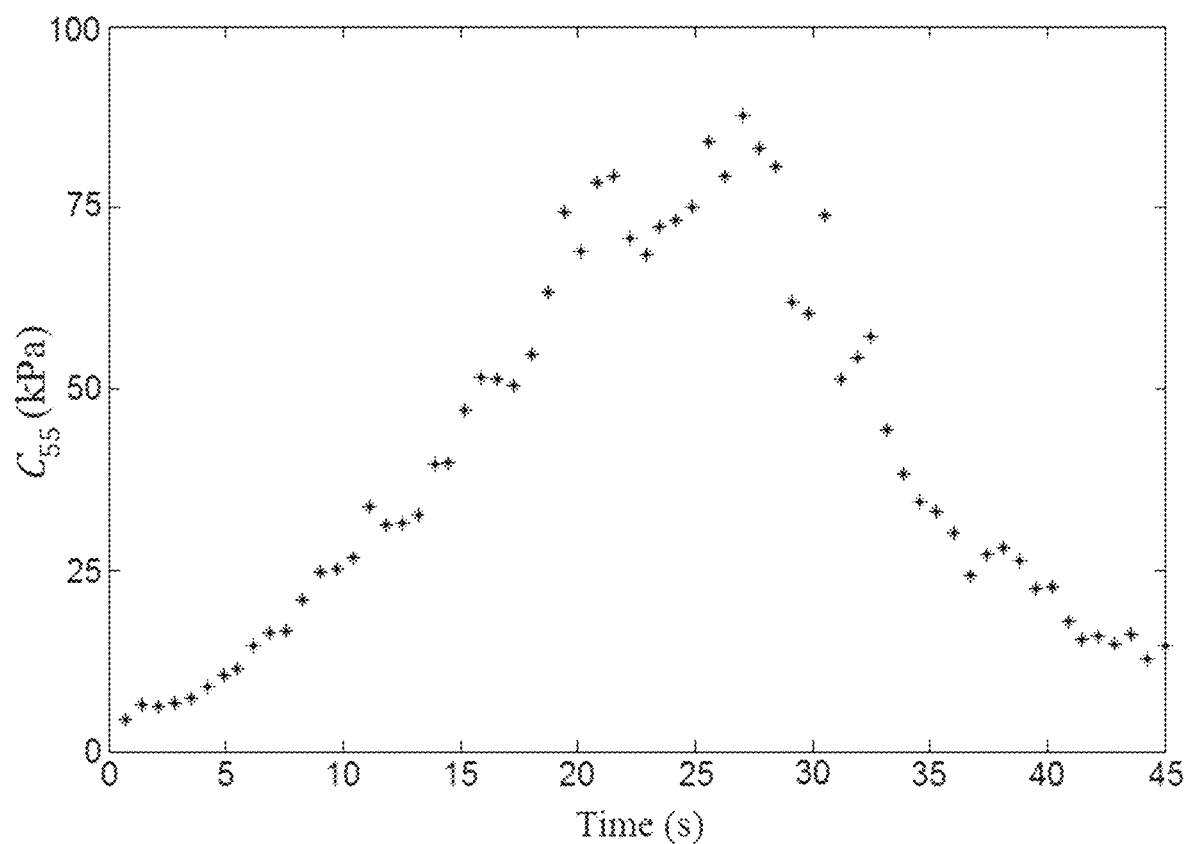
Figure 16:
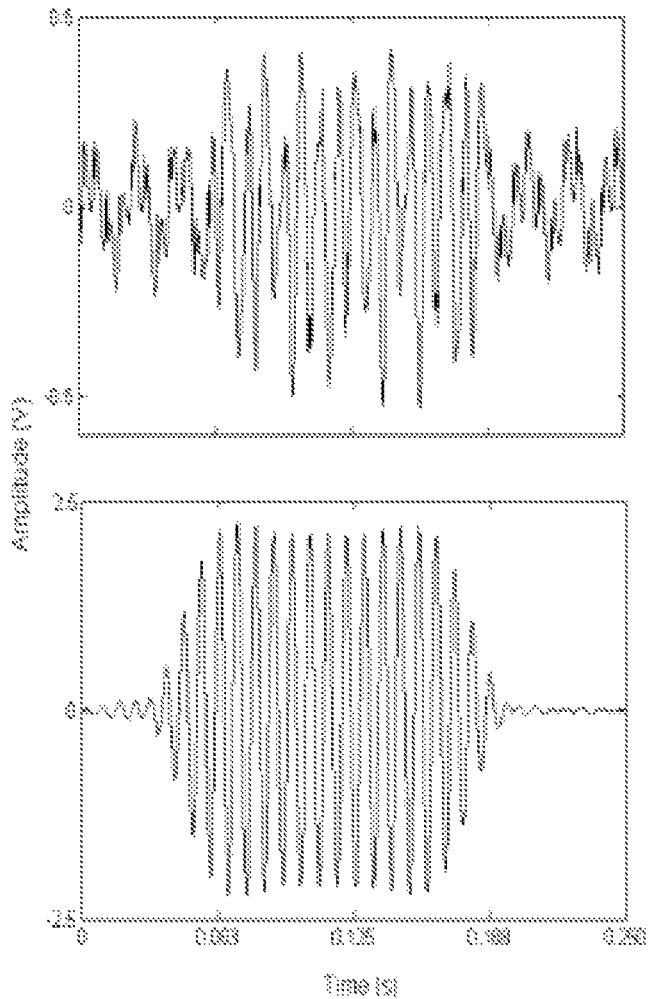
FIG. 16 illustrates an example of the time trace of a recorded signal.

Estimation of elastic properties of skeletal muscle in dynamic conditions is important in sport science to evaluate the health state of muscles. Thus, the present invention would be beneficial in this and related areas. In this example, the present invention is used to monitor changes in $c_{55}$ in biceps brachial of three healthy volunteers during isometric contraction. The volunteers were asked to contract the muscle to 40% of their maximum voluntary contraction (MVC, measured previously with an isokinetic dynamometer) in 20 seconds. Then, keep this contraction for other 5 seconds and finally reduce the contraction to 0% in 20 seconds. FIGS. 15A-15C show the obtained results for each volunteer where it can be observed that the present invention is capable of following elasticity changes in dynamic situations.

Determination of $V_T$ in Tissue Mimicking Phantoms

Figure 7:
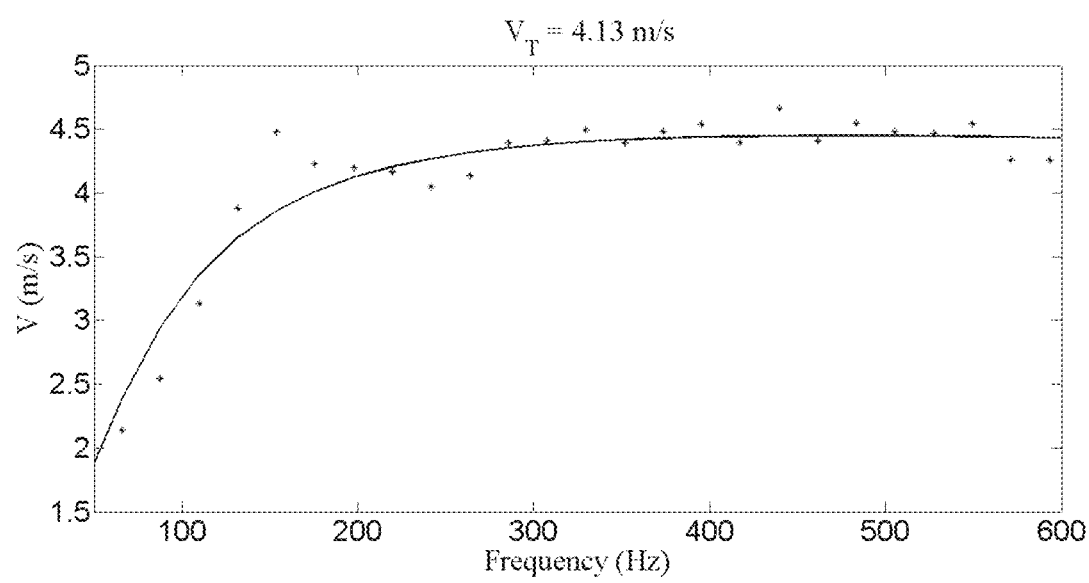
FIG. 7: shows the surface wave phase velocity measured in an isotropic solid as function of frequency for a position $x_1 < x_s$. Dots, experimental values. Full line: Inversion method #1.
Figure 8:
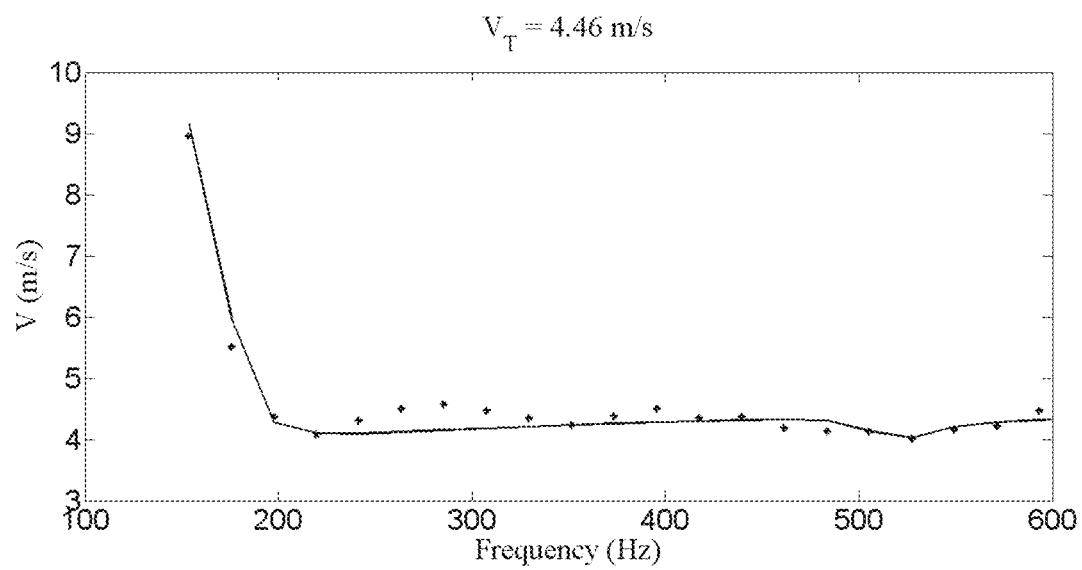
FIG. 8: shows the surface wave phase velocity measured in an isotropic solid as function of frequency for a position $x_1 \approx x_s$. Dots: experimental values. Full line: Inversion method #3.
Figure 9:
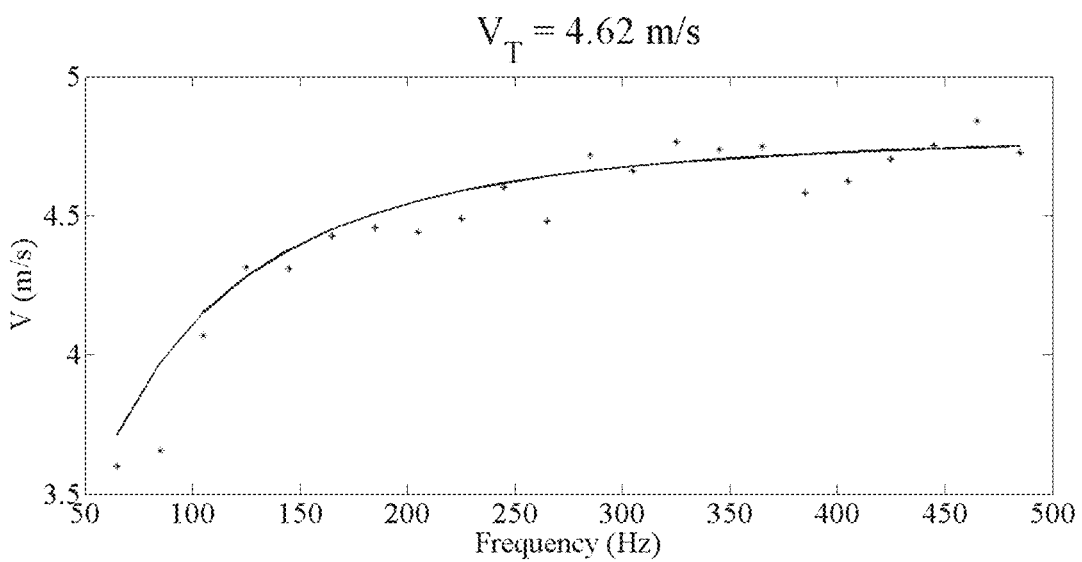
FIG. 9: shows the surface wave phase velocity measured in an isotropic solid as function of frequency for a position $x_1 > 2x_s$. Dots: Experimental values. Full line: Inversion method #4.
Figure 10:
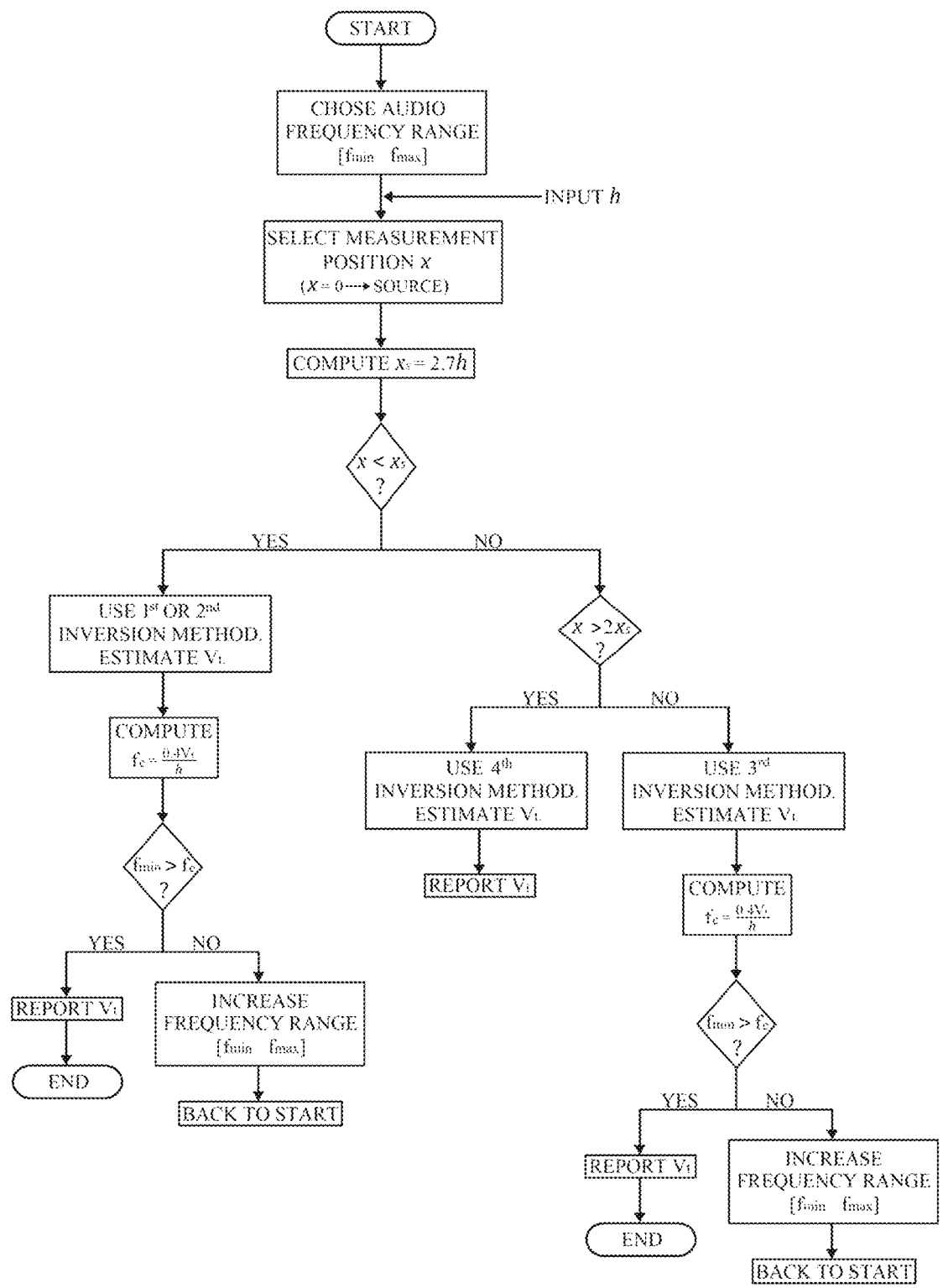
FIG. 10: is a block diagram representing the inversion algorithm for an isotropic solid.

In this section we present experimental results for the application of the present invention in agar-gelatin based phantoms (isotropic solid). These types of phantoms are widely used to simulate the mechanical properties of soft tissues. They were made from a mixture of agar (1% w/w) and gelatin (3% w/w) in hot water (>80° C.). Alcohol and antibiotics were also added for conservation purposes. Thus, we elaborated a sample with parallelepiped shape of height 2h=20 mm, long and width 100 and 120, respectively. FIGS. 7, 8 and 9 display the dispersion curve for the phase velocity of the surface wave, obtained for the configurations $x_1 < x_s$, $x_1 \approx x_s$ y $x_1 > 2x_s$, respectively. Each point of these curves was obtained by exciting the surface actuator with 6 cycles of sinusoid at the corresponding frequency. Then the phase velocity V for each receiving channel was computed. In this way, by adjusting the experimental data to the theoretical curves provided by the appropriate inversion method according to the experimental configuration, the corresponding values of $V_T$ were obtained.

The invention claimed is:

1. A method for determining the elasticity of a soft-solid, the method comprising:
    using a wave source for exciting low-amplitude audible frequency waves in a selected location of a free surface of the soft-solid whose elasticity is to be determined;
    recording the time-traces of the surface displacement with a plurality of contact vibration sensors that are linearly arranged and equally spaced to each other, wherein the distance between the point at which the waves are being excited and the nearest sensor is the same as the distance between sensors;
    computing the phase velocity of the surface wave by estimating the phase-shift between sensors and a reference signal sent to the source; and
    converting the phase velocity to an elasticity value by using an inversion algorithm,
    wherein the soft-solid is an isotropic solid, and wherein the inversion algorithm takes into account near-field effects and employs:
        a dispersion curve comprising a range of frequencies, or
        a single frequency value.

2. A method for determining the elasticity of a soft-solid, the method comprising:
    using a wave source for exciting low-amplitude audible frequency waves in a selected location of a free surface of the soft-solid whose elasticity is to be determined;
    recording the time-traces of the surface displacement with a plurality of contact vibration sensors that are linearly arranged and equally spaced to each other, wherein the distance between the point at which the waves are being excited and the nearest sensor is the same as the distance between sensors;
    computing the phase velocity of the surface wave by estimating the phase-shift between sensors and a reference signal sent to the source; and
    converting the phase velocity to an elasticity value by using an inversion algorithm,
    wherein the soft-solid is a transversely isotropic solid, and wherein the inversion algorithm takes into account near-field effects and the propagation direction of surface waves and employs:
        a dispersion curve comprising a range of frequencies, or
        a single frequency value.

* * * * *